United States Patent [19]
Harter et al.

[11] Patent Number: 5,846,411
[45] Date of Patent: Dec. 8, 1998

[54] SINGLE-PHASE FLUID DISTRIBUTOR-MIXER-EXTRACTOR FOR BEDS OF GRANULAR SOLIDS

[75] Inventors: Isabelle Harter, Lyons; Denis Darmancier, Vienne; Pierre Renard, Saint Nom la Breteche, all of France

[73] Assignee: Institute Francais du Petrole, Rueil-Malmaison, France

[21] Appl. No.: 842,427

[22] Filed: Apr. 24, 1997

Related U.S. Application Data

[62] Division of Ser. No. 572,151, filed as PCT/FR94/100968, Aug. 1, 1994.

[30] Foreign Application Priority Data

Aug. 2, 1993 [FR] France .................................. 93/09.593

[51] Int. Cl.⁶ .................................................. B01D 15/08
[52] U.S. Cl. ...................... 210/198.2; 210/283; 210/284; 210/285; 210/541; 210/656; 210/659; 96/107
[58] Field of Search .................. 210/656, 659, 210/198.2, 283, 284, 289, 285, 291, 541; 96/107

[56] References Cited

U.S. PATENT DOCUMENTS

| | | |
|---|---|---|
| 3,214,247 | 10/1965 | Broughton .............................. 210/284 |
| 3,230,167 | 1/1966 | Golay ........................................ 96/107 |
| 3,250,058 | 5/1966 | Baddour ................................... 96/107 |
| 3,374,606 | 3/1968 | Baddour ................................... 96/107 |
| 3,453,811 | 7/1969 | Crowley ................................... 96/107 |
| 3,494,103 | 2/1970 | Mir ............................................ 96/107 |
| 3,522,172 | 7/1970 | Pretorius ................................... 96/107 |
| 3,719,591 | 3/1973 | Crits ........................................ 210/283 |
| 3,948,775 | 4/1976 | Otani ...................................... 210/289 |
| 4,354,932 | 10/1982 | McNeil ................................. 210/198.2 |
| 4,400,278 | 8/1983 | Martinola .............................. 210/283 |
| 4,461,706 | 7/1984 | Siegers .................................. 210/283 |
| 4,636,315 | 1/1987 | Allen ................................... 210/198.2 |
| 4,891,133 | 1/1990 | Colvin ................................. 210/198.2 |
| 5,084,184 | 1/1992 | Burns ................................... 210/198.2 |
| 5,141,635 | 8/1992 | LePlang .............................. 210/198.2 |
| 5,200,075 | 4/1993 | Otani ................................... 210/198.2 |
| 5,316,821 | 5/1994 | Otani ................................... 210/198.2 |
| 5,324,426 | 6/1994 | Joseph ................................. 210/198.2 |
| 5,354,460 | 10/1994 | Kearnex .............................. 210/198.2 |

*Primary Examiner*—Ernest G. Therkorn
*Attorney, Agent, or Firm*—Antonelli, Terry, Stout & Kraus, LLP

[57] ABSTRACT

Disclosed is a single-phase fluid distributor-mixer-extractor for separating beds of granular solids used in chromatography. The distributor includes a device for adding or removing a secondary fluid. The distributor further includes at least one calibrated orifice having a geometry designed to create a sufficient pressure drop to confine fluid turbulence inside a mixing chamber.

5 Claims, 15 Drawing Sheets

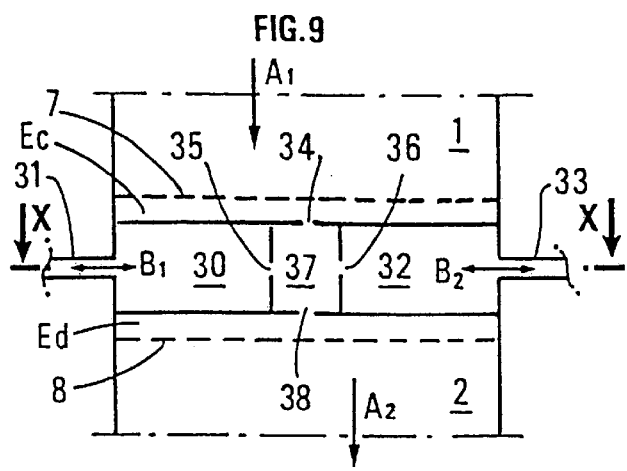
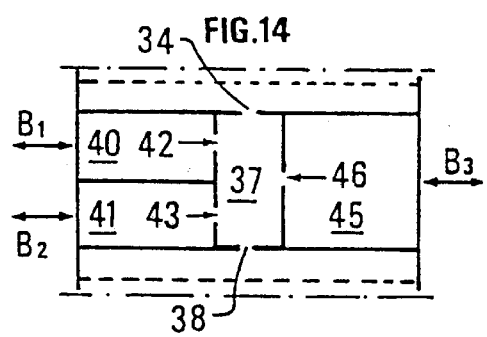
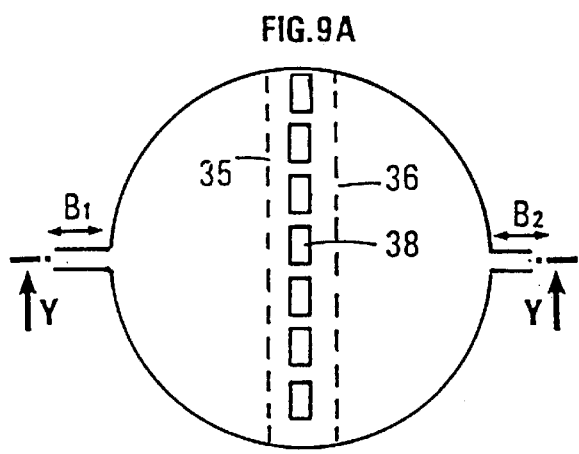
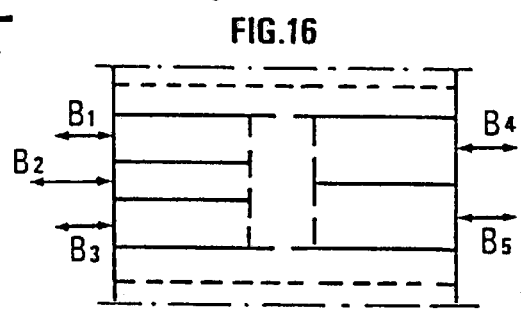
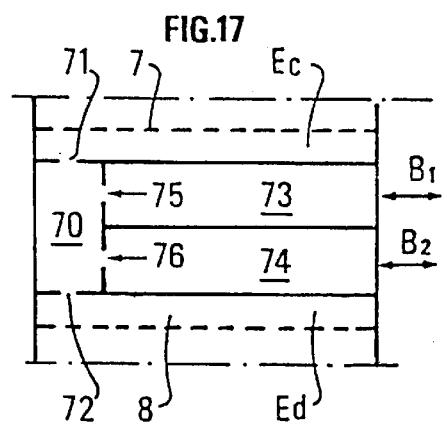
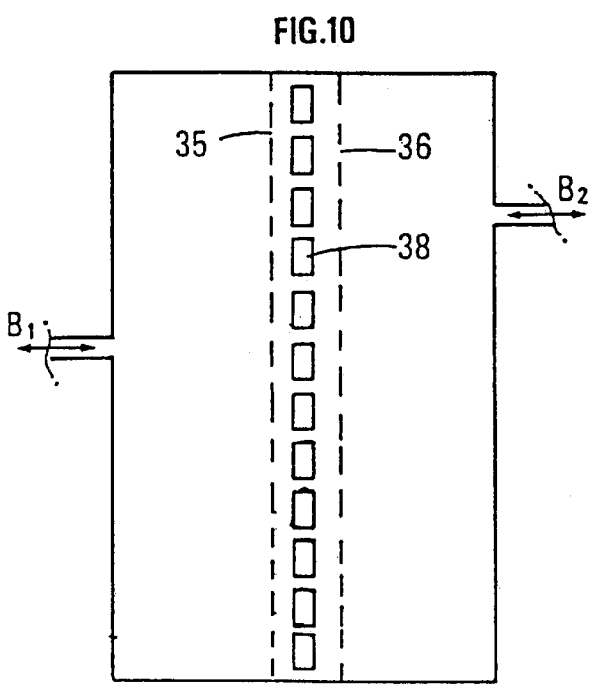

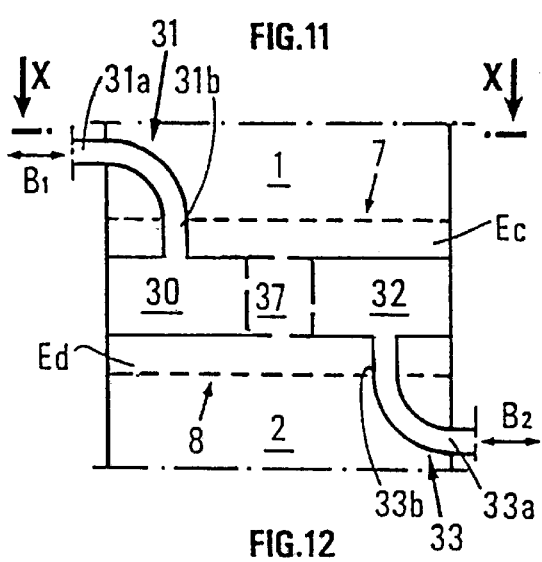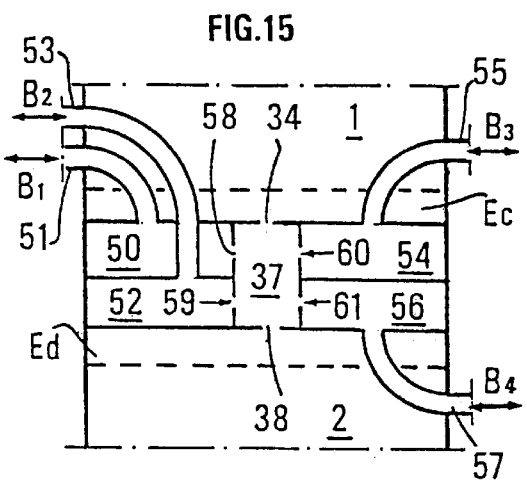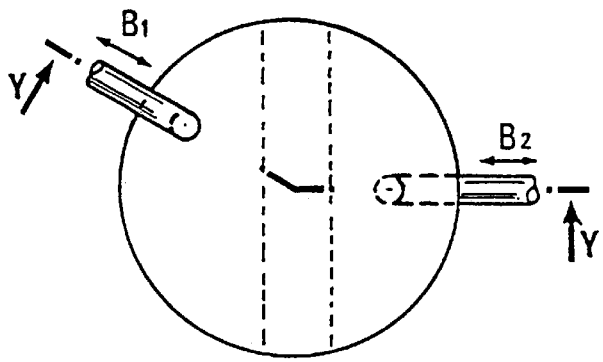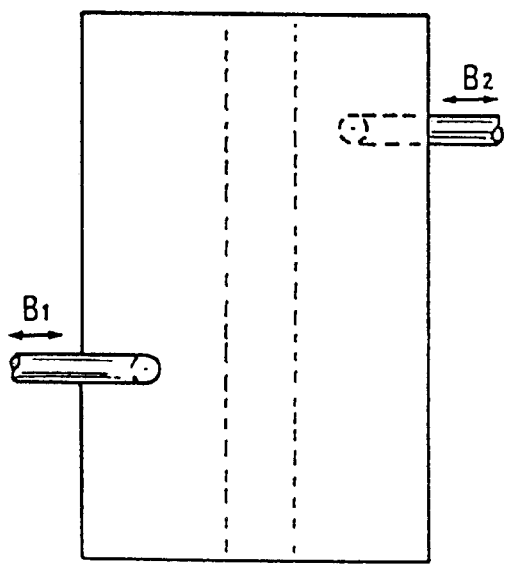

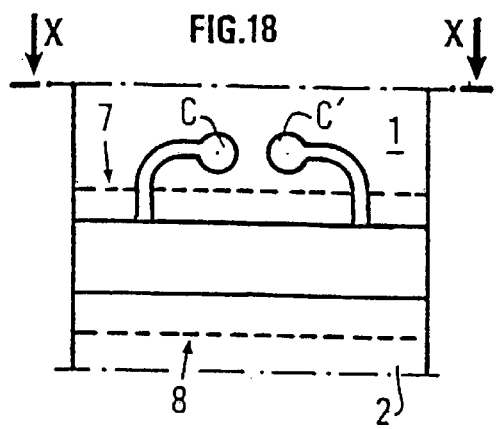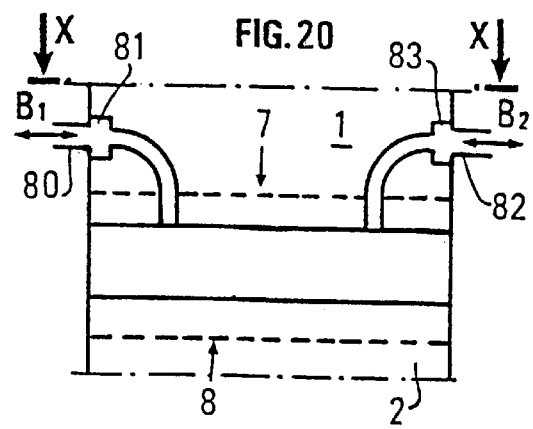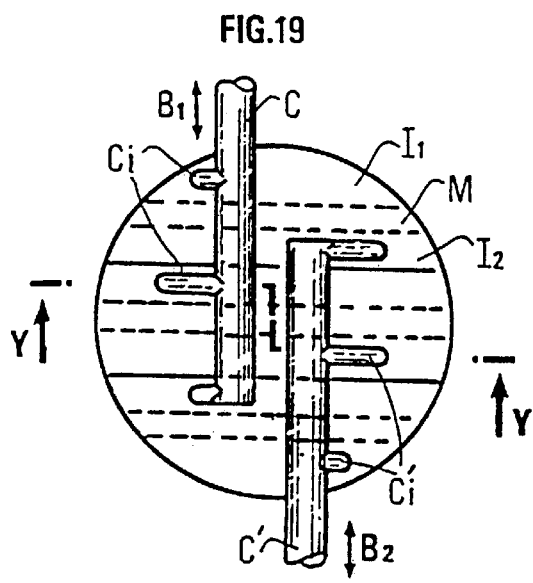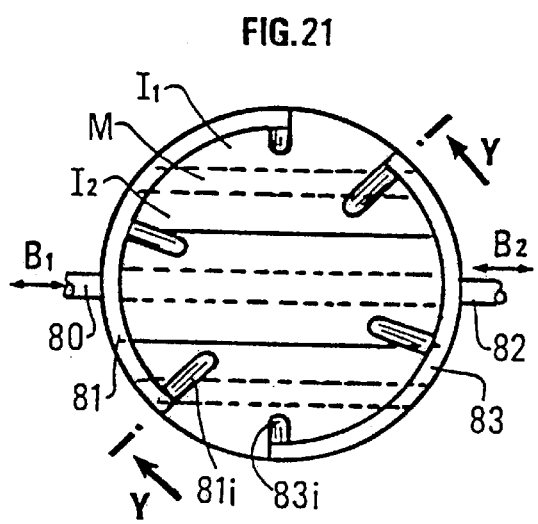

SINGLE-PHASE FLUID DISTRIBUTOR-MIXER-EXTRACTOR FOR BEDS OF GRANULAR SOLIDS

This application is a Divisional application of allowed application Ser. No. 08/572,151, filed on Nov. 22, 1995, which application is a Continuation-In-Part application of International Application No. PCT/FR94/00968, filed on Aug. 1, 1994 designating the United States.

The present invention relates to a single-phase fluid distributor-mixer-extractor (hereinafter called DME) for beds of granular solids. It applies in particular to fluids in a gaseous, liquid, or supercritical state in the field of chromatography. The present invention also relates to a column having at least two beds of granular solids separated from each other by at least DME.

In the field of distributing a fluid entering a zone and in particular entering a bed of granular solids, particularly in the field of liquid chromatography, it is important for the fluids distributed or collected to be as homogenous as possible.

Particularly in the case of simulated movable bed chromatography, often called simulated countercurrent chromatography, which usually combines large diameters and numerous separation stages with injection or removal of products between two stages, this DME must provide radial collection of a principal fluid (A) as uniformly as possible while bringing about a minimum of dead space in the chromatography column. This DME must be designed to minimize backmixing which could be detrimental to separation of the substances already effected in a zone upstream of this DME. It must also be designed so that the pressure drop DP it brings about in the column is as low as possible.

This DME must also, when at least one secondary fluid (B) is being injected, ensure as uniform as possible a mixing of this fluid (B) with fluid (A) under the same conditions as above, namely minimizing dead space, backmixing, and the pressure drop DP induced. The same applies in the case where a fluid is removed from this DME.

Finally, this DME must ensure radial redistribution of the fluid obtained after addition or removal at the inlet to the chromatography zone located immediately downstream of said DME. This redistribution must be as uniform as possible, bring about a minimum of dead space and backmixing in order not to affect separation of substances already effected in a zone upstream of this DME, and also imply the lowest possible pressure drop DP.

Among the distributor systems or DMEs described in prior publications and used industrially for specialty chemicals, laboratories, or large industries, one may cite the distributor offered by the Amicon Company which comprises a central deflector-distributor system. This distributor affords relatively correct distribution of the principal fluid with little dead space, but does not include a means for providing a secondary fluid addition or removal function nor a means providing a function whereby a secondary fluid is mixed with the principal fluid. Also, the central deflector system brings about some perturbation in radial distribution of the principal fluid and the pressure drop is relatively large because of the fast flowrates at the relatively tiny central collection point in the distributor.

It will be recalled that the terms upstream and downstream must be considered relative to the direction of fluid circulation.

U.S. Pat. No. 3,948,778 describes a DME used in a chromatography column with two beds in which the principal fluid (A) is collected downstream of a grid located at the outlet of the first bed by a channel and sent upstream of the second bed and of a collecting grid via a channel, before being redistributed into the second bed laterally. The secondary fluid (B) can be introduced via an additional channel and mixed in line with the principal fluid, with the mixing taking place at one point, relatively speaking. The collecting and redistributing zones are separated by an inclined sealed baffle. This DME allows conical collection with a low dead space. However, the manner of mixing of the two fluids is not optimal. Moreover, the existence of an outside line brings about an additional dead space which can generate a backmixing phenomenon and additional pressure drops. Lateral distribution of the fluids, due to its absence of symmetry, may bring about difficulties of implementation and imperfect homogenization for large diameters.

The DME described in U.S. Pat. No. 3,214,247 is used in a chromatography column. The principal fluid is collected in totality downstream of a collecting grid positioned at the outlet of a first bed and redistributed downstream of a grid located in the vicinity of a second bed. The secondary fluid is introduced through holes positioned in the central zone of the DME where it mixes directly with the principal fluid. This DME has the advantage of having little dead space and bringing about a relatively moderate pressure drop because of its transverse collection. However, the mixing function is not totally controlled and may bring about backmixing phenomena throughout the conical collecting and/or redistributing section. Moreover, the mixing zone is not confined to the central zone according to one diameter.

The present invention remedies the aforementioned drawbacks and at the same time meets the objectives in view by using a DME that in particular ensures very good mixing of the principal and secondary fluids.

The invention relates to a fluid distributor-mixer-extractor designed to be placed in a column between a first and a second bed of granular solids, comprising in combination:

at least one injection and/or removal channel of a secondary fluid or second fluid, said channel being connected to at least one injection or removal chamber or first chamber, said first chamber having at least one passage opening in at least one of its walls, one or more means for collecting a principal fluid, at least one mixing chamber or second chamber located in the vicinity of said first chamber and communicating with the latter by at least one passage opening, said second chamber having one or more orifices allowing passage of said second fluid coming from said collecting means or to said collecting means and at least one passage for a fluid coming from the mixing chamber, at least one or more means of redistributing said fluid coming from said mixing chamber to the second bed of granular solids, a baffle located:

relative to the collecting means and to the mixing chamber to create a collecting space communicating with said opening, relative to said redistributing means and to said mixing chamber to create a space for redistributing said fluid coming from the mixing chamber, said redistributing space communicating with said passage, and said baffle being located such as to separate said collecting and redistributing spaces.

The distributor-mixer-extractor is characterized in that at least one of the fluid passages has at least one calibrated orifice having a geometry designed to create a sufficient pressure drop to confine fluid turbulence inside said mixing chamber.

The cross section of the calibrated orifices is chosen such that the flowrate of the fluid passing from the mixing chamber to redistributing space Ed is between 1 and 5 m/s, the means by which the principal fluid is introduced from collecting space Ec to the mixing chamber having orifices whose cross section is such that the flowrate of the principal fluid is between 1 and 5 m/s and so that the secondary fluid passage means has orifices whose cross section is chosen so that flowrate of each secondary fluid to or from the mixing chamber through these orifices is between 1 and 15 m/s.

The redistributing means comprises a grid extending essentially over the entire section of the column.

The distributor-mixer-extractor has at least two injection and/or removal chambers each connected to a channel for injection and/or removal of a second fluid, the chambers having at least one orifice, the axes of the orifices being staggered with respect to each other to prevent passage of fluids coming from one of the injection and/or removal chambers to another injection and/or removal chamber.

The distributor-mixer-extractor has at least two injection and/or removal chambers, the collecting and/or removal chambers being disposed one above the other and on the same side as one of the walls of the mixing and/or removal chamber, the mixing and/or removal chamber having one wall in common with said column or the edge of the DME.

The distributor-mixer-extractor has four injection and/or removal chambers each connected to a secondary fluid injection and/or removal channel, the chambers being disposed two-by-two on each side of the mixing and/or removal chamber.

The distributor-mixer-extractor has five injection and/or removal chambers disposed on either side of the mixing chamber.

The secondary fluid introduction and/or removal channels are arranged with respect to the column to introduce and/or remove a secondary fluid into or from the injection and/or removal chamber in a direction essentially parallel to a first grid included in the collecting means.

The secondary fluid introduction and/or removal channels are arranged relative to the column for introducing and/or removing the secondary fluid or fluids into or from the injection and/or removal chamber in a direction essentially perpendicular to the collecting means comprising a grid.

The calibrated orifices and the openings through which the secondary fluid or fluids passes or pass to or from the mixing chamber are disposed at the level of the mixing chamber to allow introduction of said second fluid and/or its extraction in a direction essentially perpendicular to the fluid outlets through the passage.

The openings are located on at least one first mixing chamber wall, and the outlet passages on at least one other of the walls of the mixing chamber and the openings and outlet passages are disposed alternately with respect to each other.

The means of introduction and passage means for the secondary fluid are disposed respectively relative to the mixing chamber to allow circulation of fluids in directions essentially parallel with each other, in opposite directions.

The passages means and the passage means for the secondary fluid are disposed respectively relative to the second chamber and relative to the first chamber to allow circulation of the second fluid and the first fluid in directions essentially perpendicular to each other.

The shape of the baffle is designed so that the collecting and redistributing spaces are substantially frustroconical, with the bases of the spaces being supported by one of the walls of the column and with the spaces communicating with each other through their narrowest opening in the vicinity of the collecting chamber.

The shape of the baffle and its location in the column are chosen to isolate the collecting and redistributing spaces.

The baffle extends from the periphery of the column up to at least the mixing and/or removal chamber.

The baffle has at least one series of orifices, the orifices communicating with the mixing and/or removal chamber orifices and the baffle extending essentially over the entire cross section of the column.

The baffle is self-supporting and has a thickness of between 5 and 50 mm and preferably between 12 and 20 mm.

The mixing chamber has means for favoring turbulence.

The present invention also relates to a column having at least one first bed and at least one second bed of granular solids separated from each other by at least one distributor-mixer-extractor wherein the first grid is substantially in contact with the first bed and the second grid is substantially in contact with the second bed.

The first and second grids cover respectively essentially the totality of the section of the first bed and essentially the totality of the section of the second bed.

According to one embodiment, the channel has several distributor-mixer-extractors and the injection and/or removal channels connecting each of the injection and/or removal chambers join in a principal channel inside said column.

The column has one or more distributor-mixer-extractors and each distributor-mixer-extractor has at least one external support means embedded in the bed of granular solids downstream of the second grid of the distributor-mixer-extractor.

The external support means is of the slatted type or the like.

In the remainder of the specification, the term DME will designate the distributor-mixer-extractor.

BRIEF DESCRIPTION OF THE DRAWINGS

The invention and its characteristics will be better understood by reading the following description, to which is attached figures that represent respectively:

FIGS. 9, 9A, and 10 show schematically a DME according to the invention having several secondary fluid injection and/or removal circuits, FIGS. 11, 12, and 13 show other embodiments of the invention relating to the disposition of the secondary fluid injection and/or removal channels, FIGS. 14, 15, and 16 show two examples of DMEs according to the invention having several independent injection and/or removal circuits, FIG. 17 shows one alternative embodiment for which the various secondary fluid injection and/or removal circuits are positioned on the same side of the mixing chamber, FIGS. 18, 19, 20 and 21 show alternative embodiments of injection circuits in the case of a column with several DMEs.

DESCRIPTION OF THE PREFERRED EMBODIMENTS

Figure 1:
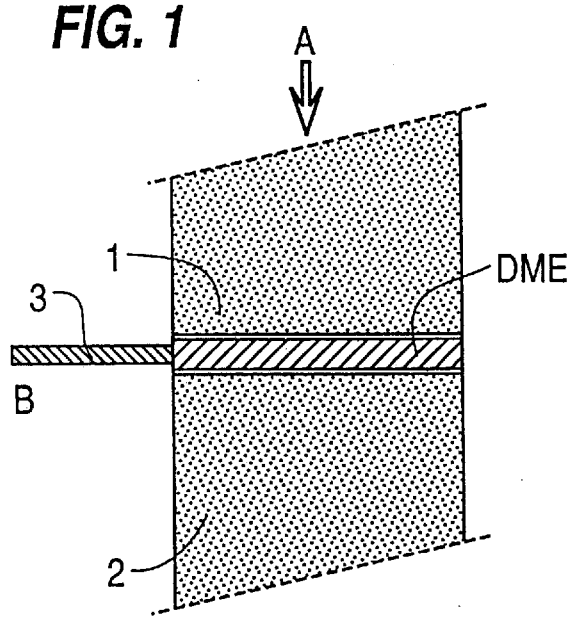
FIGS. 1 and 2 show schematically the utilization principle of a distributor-mixer-extractor or DME.
Figure 2:
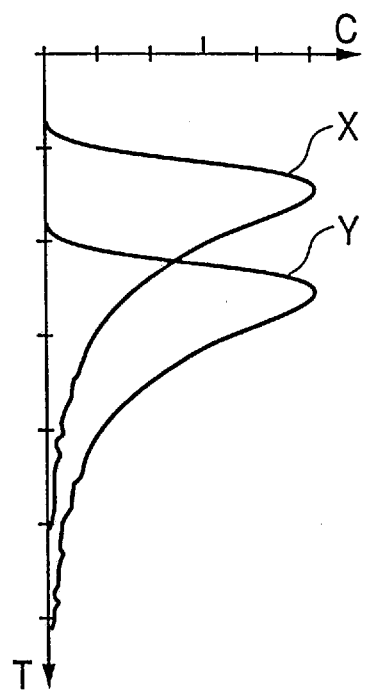

For better understanding of the invention, the principle of a distributor-mixer-extractor is called to mind briefly in FIGS. 1 and 2. FIG. 1 is a cross section through part of a chromatography column with two beds 1 and 2 separated by a DME. The DME has a channel 3 for introduction of at least one secondary fluid (B) or removal of at least one fluid. A principal fluid (A) circulates downward in the direction of the arrow in the chromatography column, namely from first bed 1 to second bed 2. The role of the DME is in particular to ensure transfer of principal fluid (A) from first bed 1 or zone 1 to second bed 2 or zone 2 with the smallest possible effect on the axial concentration profiles of the fluids while permitting, for example, addition or sampling of at least one secondary fluid (B), remaining within a reasonable pressure drop range.

The description hereinbelow is particularly appropriate when the principal single-phase fluid usually used for this type of DME is in the form of a vapor or a liquid. It may also be in a supercritical state.

The curves of FIG. 2 show a typical example of axial concentration of two substances X and Y that are to be separated from a mixture containing them, with the abscissa axis representing time and the ordinate axis representing the concentration of the products to be separated.

Figure 3:
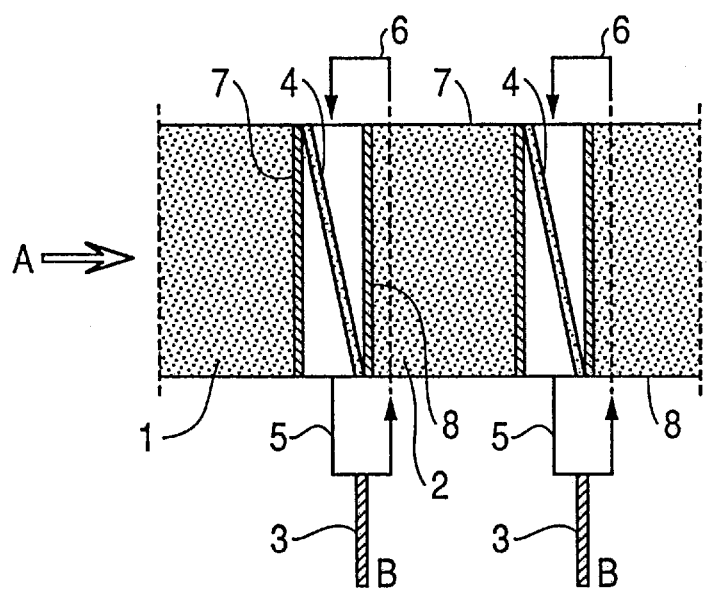
FIGS. 3, 4A and 4B are cross sections and horizontal sections through the DME according to the prior art.
Figure 4A:
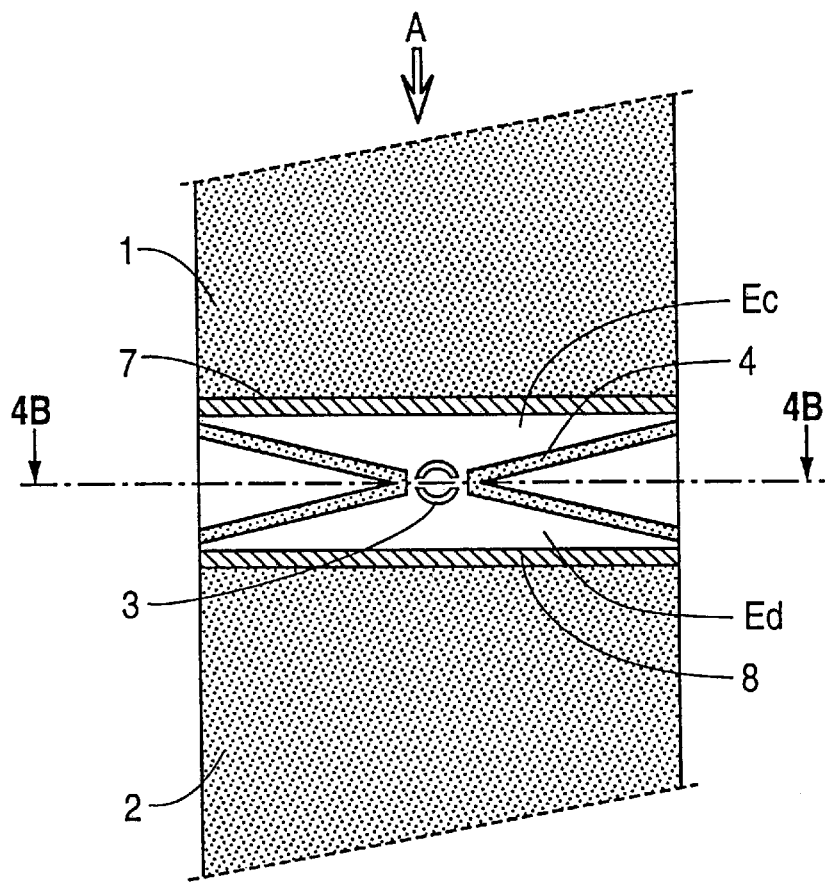
Figure 4B:
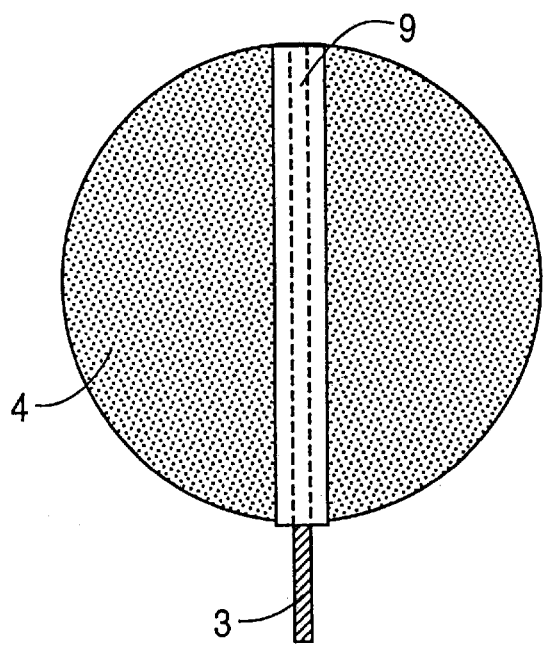

FIGS. 3, 4$a$ and 4$b$ show chromatography columns according to the prior art with two beds 1 and 2 separated by a DME having a channel 3 for introducing a secondary fluid (B). Principal fluid (A) circulates (FIG. 3) in the direction of the arrow from the first bed to the second bed.

In the embodiment of FIG. 3, the column has several beds or zones 1 and 2 separated by a DME. The DME has a grid 7 located at the outlet of zone 1 and a grid 8 located upstream of zone 2. Principal fluid (A) circulating from zone 1 to zone 2 is collected downstream of grid 7 by a channel 5 and sent upstream of grid 8 by a channel 6 in order to be redistributed in zone 2. Channel 3 allows introduction of secondary fluid (B) and its in-line mixing with principal fluid (A), for example in channel 5. The collecting and redistributing zones are separated by an inclined sealed baffle 4 in the DME as shown schematically in the figure. This embodiment allows conical collection due to the inclination of the baffle with little dead space. Nonetheless, the mixing of the two mixtures at one point, relatively speaking, is not optimal and lateral distribution of the fluids through channels 3 and 5 exhibits a lack of symmetry that may lead to difficult and nonhomogeneous distribution for beds with large diameters.

In the case of the DME shown in FIGS. 4$a$ and 4$b$, principal fluid (A) is collected downstream of grid 7 at the outlet from zone 1 and redistributed upstream of grid 8 in zone 2. The fluid introduction channel 3 is disposed such as to allow transverse introduction of the secondary fluid according to one diameter in the central zone of the column. The secondary fluid is introduced through holes 9 located essentially in the central zone where it mixes directly with the principal fluid. The baffle 4, in this embodiment, extends from the periphery of the column up to near the secondary fluid introduction or fluid collecting channel.

Such a DME has the advantage of offering little dead space and bringing about a relatively moderate pressure drop. Nonetheless, the mixing function is not totally controlled and easily brings about a backmixing phenomenon in the collecting and/or redistributing zones in a conical section, as the mixing zone is not confined to the diametrically disposed central zone.

Figure 5A:
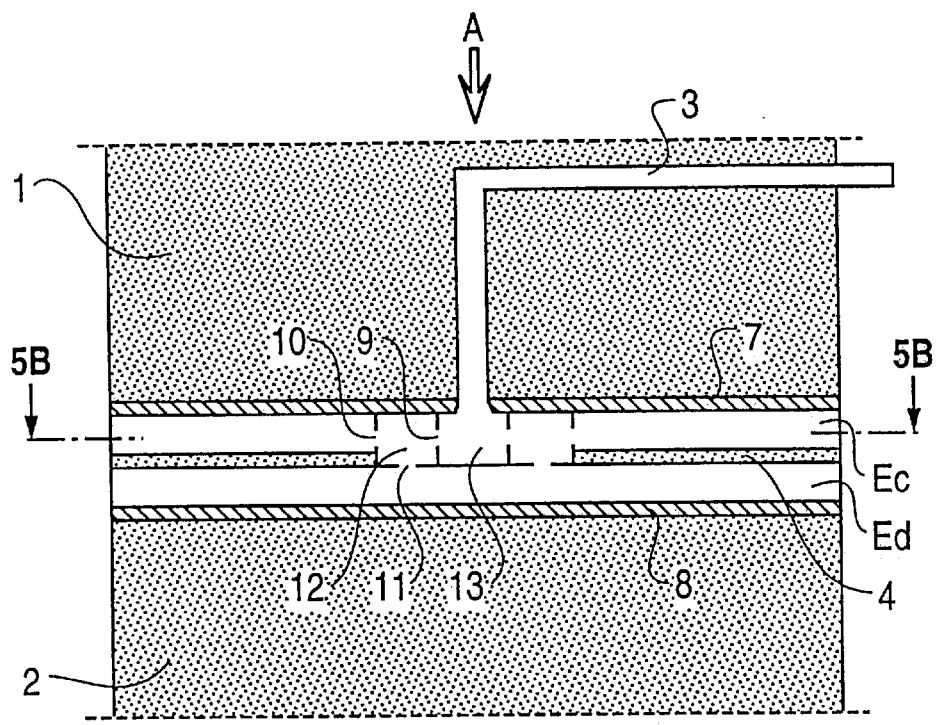
FIGS. 5A, 5B, 5C, 5D, and 5E represent one DME example according to the invention positioned between two beds of granular solids, FIG. 6 show the DME having a mixing chamber of circular shape.
Figure 5B:
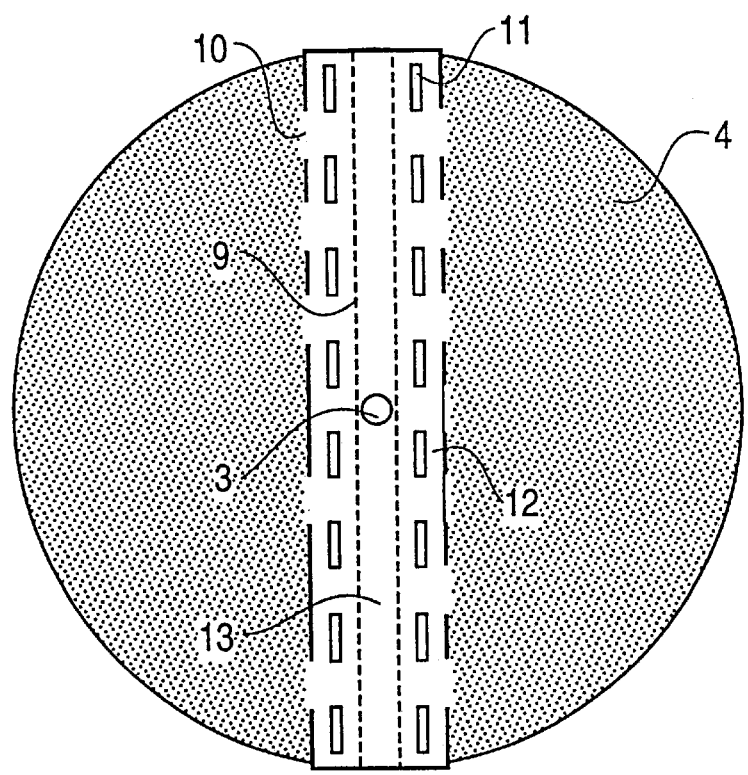

FIG. 5A shows a column having a distributor-mixer-extractor or DME according to the invention positioned between a first bed of granular solids 1 and a second bed of granular solids 2 or zones 1 and 2. This DME has at least one means of collecting at least one principal fluid (A) comprising for example a first grid 7 positioned preferably at the outlet of zone 1 and downstream of this collecting means in the principal fluid circulation direction, and at least one fluid redistributing means comprising for example a grid 8 positioned substantially parallel to grid 7. Grid 8 is located for example upstream of zone 2. The DME has for example, substantially at its center, two mixing chambers 2 with a substantially elongate rectangular shape (FIG. 5B). Each of chambers 12 has at least one means 10 of introducing principal fluid (A), for example a series of calibrated orifices or openings 10 such as slots (FIGS. 5B, 5C) located for example on one side of chamber 12, and allowing the principal fluid to enter upstream of baffle 4 in the circulation direction of principal fluid (A) and an outlet passage 11 having at least one calibrated orifice 11 such as a slot or several slots located in the lower part of the chamber for example, allowing a fluid to exit downstream of baffle 4. An injection and/or removal chamber 13 is located for example in contact and between the two mixing chambers 12 and has for example a substantially elongate rectangular shape. The injection and/or removal chamber 13 is connected to a means 3 for injecting or recovering a secondary fluid (B) such as a channel which laterally traverses zone 1 from its periphery to its central part, then extends lengthwise from the central part to injection and/or removal chamber 13 at which it terminates. Injection chamber 13 has at least one means 9 allowing secondary fluid to pass from mixing chamber 12 to injection chamber 13, such as a series of calibrated orifices. A sealed baffle 4 is positioned in the DME parallel to grids 7 and 8, for example, and extends from the periphery of the DME up to at least the injection and/or removal chamber.

Grid 7, one mixing chamber 12, and baffle 4 delimit a collecting space Ec.

In an identical manner, grid 8, baffle 4, mixing chamber 12, and injection chamber 13 delimit a redistribution space Ed.

Baffle 4 is for example placed between mixing chamber 12 and the column in order to isolate the collecting and redistribution spaces (Ec, Ed from each other.

The dimensions and distribution of orifices 10 introducing principal fluid (A), the fluid outlet orifices from the mixing chamber, and orifices 9 are preferably chosen to obtain a pressure drop and a sufficient flowrate to generate turbulence in mixing chamber 12 corresponding to strong backmixing and thus obtain better mixing efficiency of principal fluid (A) and secondary fluid (B). Such an arrangement allows mixing chamber 12 to be isolated from the collecting and redistribution spaces.

Thus, inlet orifices 10 are series of holes or slots, preferably regularly spaced to collect principal fluid (A) in the direction of mixing chamber 12 as uniformly as possible.

The dimensions and geometries of these orifices are chosen such that the fluid entering the mixing chamber has a flowrate favorable to creation of turbulence inside the mixing chamber and at the same time generate a pressure drop allowing turbulence to be confined within the mixing chamber.

Thus the space between fluid inlet orifices 10 is, for example, between 30 and 150 mm and preferably between 50 and 100 mm. The fluid flowrate through the orifices obtained with such a spacing varies for example between 1 and 5 m/s and preferably between 2 and 3 m/s. The pressure drop thus generated at the orifice exit is between 10 and 100 g/cm$^2$ and preferably between 30 and 60 g/cm$^2$.

The outlet orifices 11 of a fluid from the mixing chamber are, for example, formed by a series of holes or slots, preferably regularly spaced to distribute the fluid from the mixing chamber and resulting in most cases from the mixing of at least one principal fluid with at least one secondary fluid in the most uniform manner possible toward redistribution space Ed.

The dimensions of the holes or slots are chosen, for example, to generate a certain pressure drop enabling turbulence to be confined within mixing chamber 12, for example a pressure drop between 10 and 100 g/cm$^2$ and preferably between 30 and 60 g/cm$^2$. This pressure drop value corresponds in particular to a hole or slot spacing of 30 to 150 mm and preferably 50 to 100 mm and to a fluid flowrate exiting the mixing chamber of between 1 and 5 m/s, preferably between 2 and 3 m/s.

Orifices 9 through which the secondary fluid is introduced or removed are for example formed by a series of holes, preferably regularly spaced, to inject and/or remove secondary fluid B in the most uniform manner possible to and/or from mixing chamber 12. These orifices are for example dimensioned so that the linear flowrate of the fluid injected into the mixing chamber is sufficiently high to favor creation of turbulence in the mixing chamber and to obtain a significant pressure drop allowing secondary fluid B to be distributed and/or removed as uniformly as possible throughout the length of the injection and/or removal chamber.

The fluid flowrate through introduction or removal orifices 9 is for example between 1 and 15 m/s, preferably between 5 and 10 m/s. The hole spacing is chosen for example between 30 and 150 mm and preferably between 50 and 100 mm. The corresponding pressure drop ranges between 100 and 2000 cm/$^2$ and preferably between 200 and 1000 g/cm$^2$.

In this way, collecting, mixing, and proper distributing of the fluid coming from the mixing chamber and passing into the redistributing space at grid 8 is optimized.

Collecting space Ec located under collecting grid 7 has a shape designed to minimize dead space and fluid turbulence. Its height ranges from 5 to 50 mm for example, preferably from 5 to 30 mm, and its shape is substantially rectangular, conical, or in the form of a bowl.

Redistributing space Ed is, identically, designed to minimize dead space and turbulence. Its height ranges between 5 and 50 mm for example and preferably between 5 and 30 mm and preferably between 50 and 20 mm and it can have any shape, for example rectangular, conical, or bowl-shaped.

A mixing chamber 12 has for example an elongate and preferably rectangular shape.

The space of the mixing chamber is designed to minimize dead space. Thus, in this embodiment, its dimensions are for example chosen from the following values: its height ranges between 5 and 150 mm and preferably between 15 and 100 mm, its width between 15 and 100 mm, preferably between 25 and 80 mm and preferably between 20 and 70 mm and its length ranges between 0.5 and 5 m, preferably between 1.5 and 3 m and preferably between 1 and 4 m.

According to substantially identical criteria, injection chamber 13 has for example a substantially elongate shape, and is of the same length as the mixing chamber. It has geometric characteristics chosen from the following group of values: a height of between 5 and 150 mm and preferably between 15 and 100 mm, a width between 15 and 100 mm and preferably between 20 and 80 mm and preferably between 25 and 70 mm. The cross-section of the chamber is designed to obtain a linear lengthwise flowrate less than or equal to a value preferably between 2 and 5 m/s.

The mixing chambers are placed for example directly in contact with grid 7 and occupy for example a space with a height less than or equal to the distance separating grids 7 and 8.

They can also occupy a space with a height preferably substantially equal to the distance separating grid 7 and baffle 4.

Figure 5C:
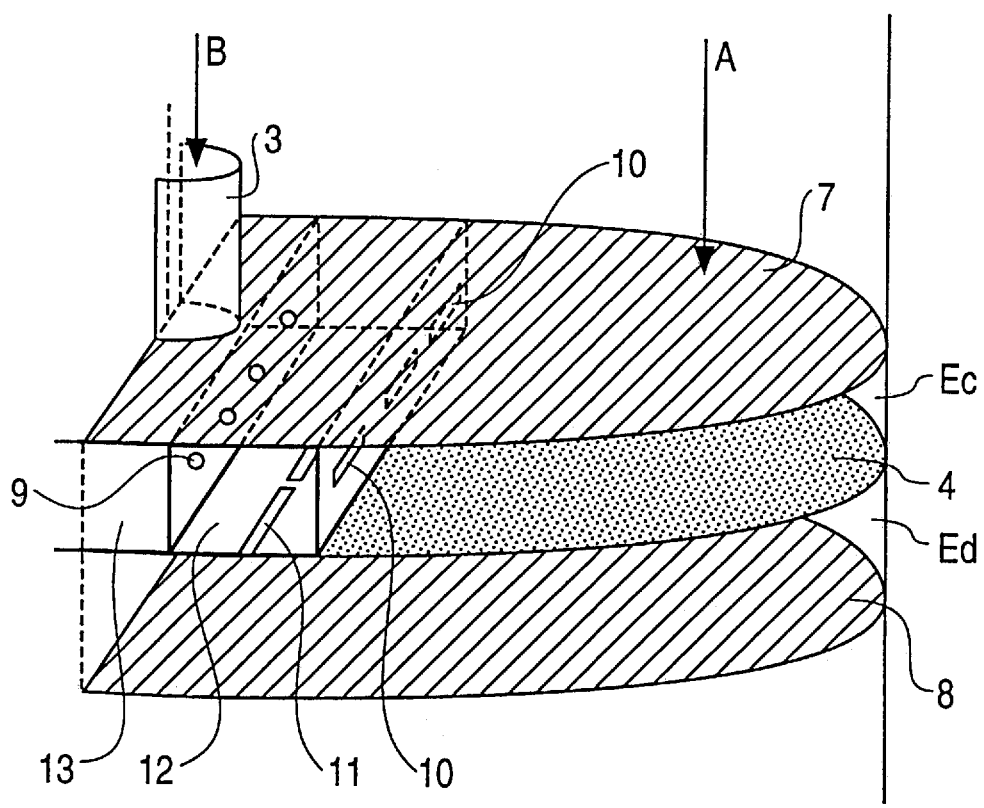

According to one embodiment, the arrangement in series of slots 10 and 11 allows for example collection and distribution of principal fluid A and distribution of the fluid from mixing chamber 12 in directions for example substantially perpendicular to each other (FIGS. 5A, 5C). The series of slots are preferably disposed in a staggered arrangement (FIGS. 5B, 5C).

Orifices 9 or the series of orifices for passage of the secondary fluid into the mixing chamber are for example located on one of the sides of chamber 13 (FIG. 5A) such as to allow circulation of fluids between the two chambers in directions substantially parallel to each other in opposite directions.

Collecting grid 7 is preferably substantially horizontal and positioned directly in contact with the first granular bed or upper bed and covers preferably substantially the entire cross section of this bed.

Distributing grid 8 is located for example substantially horizontally and is located immediately in contact with the second granular bed or lower bed. The grid extends preferably over practically the entire cross section the second granular bed.

Grids 7 and 8 are, in most embodiments, Johnson grids or grids of an equivalent type. These grids usually have slots with a width of approximately 0.1 mm to approximately 1 mm and usually a width of approximately 0.1 mm to approximately 0.20 mm.

Although this is not shown in the attached figures, it is possible to add, within mixing chamber 12, at least one means for promoting turbulence of the fluids entering this chamber. Thus the chamber is equipped for example and preferably with a series of turbulence-promoting means such as internal baffles designed to increase mixing efficiency. This mixing chamber 12a preferably has as small a volume as possible in order to minimize backmixing.

Injection or removal channel 3 allows at least one secondary fluid (B) to be introduced and/or recovered into or from the chamber in a direction perpendicular to the plane of grid 7.

According to another embodiment, not shown schematically, injection channel 3 allows at least one secondary fluid (B) to be introduced into and/or removed from the distributing chamber and/or collecting chamber in a direction parallel to the plane of grid 7.

It will not be a departure from the invention if chamber 12 is not attached to grid 7.

Figure 5D:
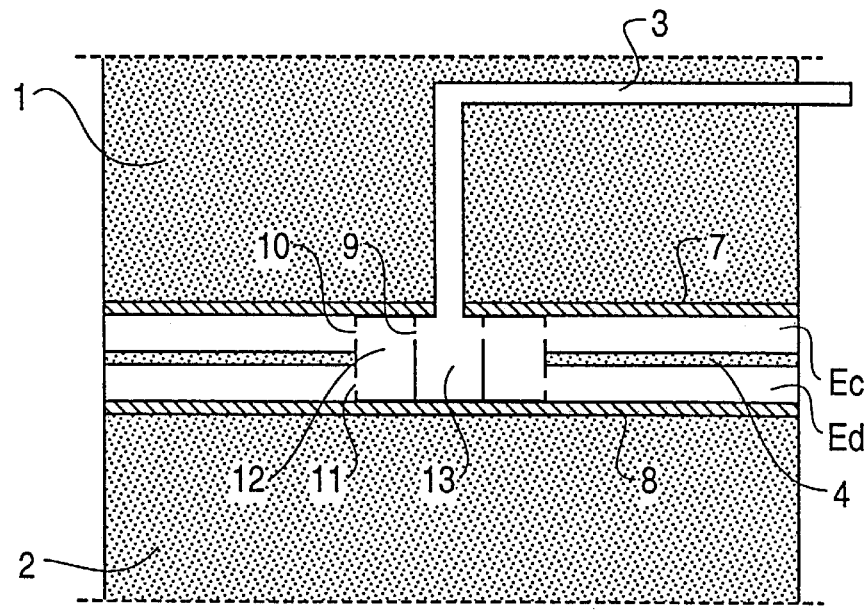

According to another embodiment (FIG. 5D), chamber 12 occupies a volume with a height substantially equal to the distance separating grids 7 and 8. The series of means 11, in this figure, allow collection and distribution of fluids directions substantially parallel with each other.

In the embodiments of the DME shown according to FIGS. 5A, 5B, 5C, 5D, and 5E, the injection or removal means 3 is a simple channel, but any other injection means fulfilling the same function can be used. Thus, when several secondary fluids are injected or recovered in the same DME, the DME has for example several channels terminating in the same chamber 13. It is also possible to have, at the start, several channels joining each other to form a single channel terminating in chamber 13, these embodiments not being shown in the figures with a view to simplification.

Figure 5E:
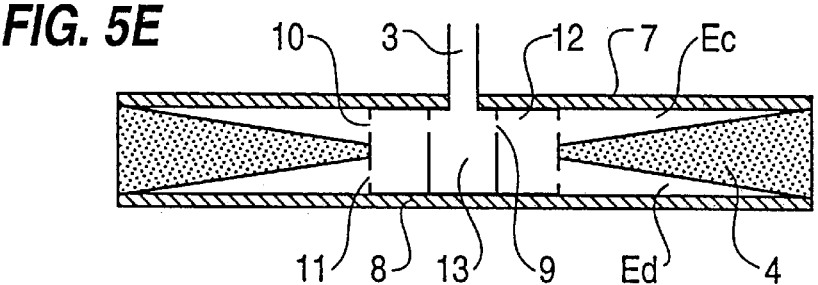

FIG. 5E shows a preferred embodiment wherein baffle 4 has a shape such that it creates, between grid 7, the periphery of the DME, mixing chamber 12, and itself, a collecting space Ec that is substantially conical or frustroconical and between grid 8, the periphery of the DME, the mixing chamber, and itself a conical or frustroconical redistributing space Ed. The tip of the cone thus formed is located at the level of the mixing chamber. This embodiment offers the advantage of significantly minimizing dead space and obtaining an induced pressure drop that remains small, and between grid 8, the periphery of the DME, the mixing and/or removal chamber 12, and itself an essentially conical space.

Figure 6:
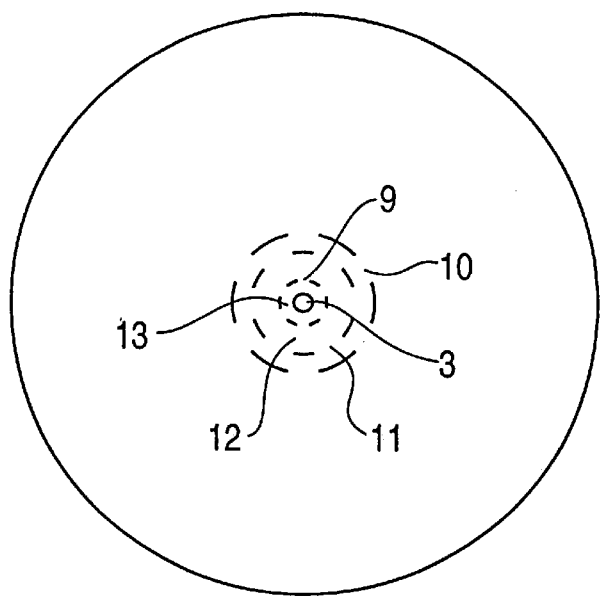

FIG. 6 shows a horizontal section through one embodiment of a DME according to the invention wherein the cross sections of chambers 12 and 13 have substantially circular shapes.

Mixing chamber 12 and distributing chamber 13 are concentric, the distributing chamber being for example positioned inside distributing chamber 12.

The present invention also relates to a column having at least two granular solids beds separated from each other by at least one DME as described above. This design is for example shown schematically in FIG. 8A in the case of a column with two granular solids beds separated by a DME. Existing DMEs of the prior art are usually designed to be self-supporting, namely they have an internal self-supporting structure of the slatted type for example which has the drawback of creating an additional dead space harmful to DME performance.

Figure 7:
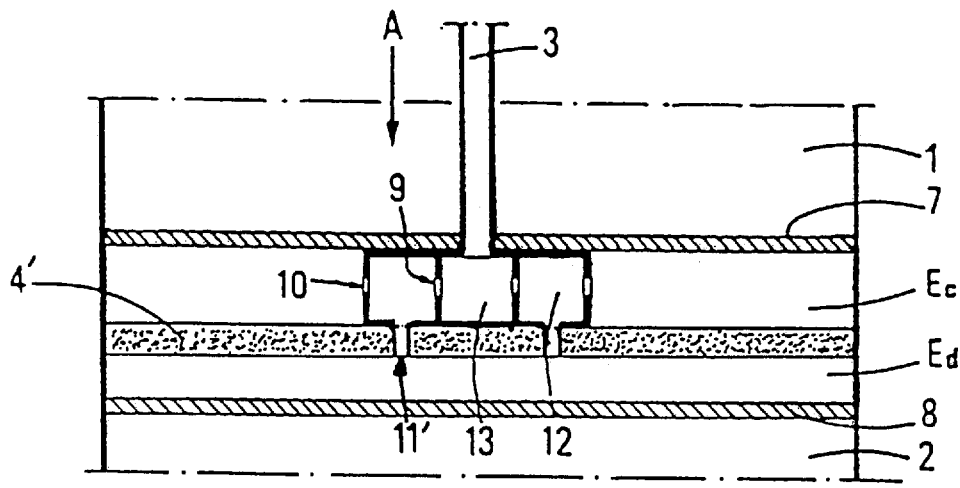
FIG. 7 shows schematically one embodiment according to the invention having a self-supporting structure.

In a preferred embodiment (FIG. 7), the DME can be designed with a built-in self-supporting structure that creates no dead space like the slatted support used in the prior art. In this case, the rigidity and mechanical strength of a self-supporting baffle 4' afforded by a substantial thickness are used, this baffle being preferably disposed over the entire cross section of the DME.

Such an embodiment offers in particular the possibility of increasing the thickness of the self-supporting baffle in order to obtain greater mechanical strength while retaining the same mixing and redistributing qualities of the DME without bringing about additional dead space. The DME design is also simplified thereby.

The thickness of the self-supporting baffle is for example between 5 and 50 mm, preferably between 10 and 30 mm and preferably between 12 and 20 mm.

The shape and arrangement of mixing chamber 12 and injection chamber 13 can be identical to the shapes described in relation to the foregoing figures and in this embodiment are located directly on baffle 4'. The distributing orifices 11' allowing fluid to pass from mixing chambers 12 to redistributing space Ed have substantially identical geometric characteristics to those of the previously mentioned orifices 11.

The lower walls of mixing chamber 12 and/or injection chamber 13 can be formed by part of self-supporting baffle 4'.

According to another embodiment, the DME is made for example without a self-supporting internal structure and is designed to withstand compressive forces; in this case, the DME is supported by a bearing structure or external support means embedded in the granular solids bed of the slatted type or the equivalent for example. Such a DME has the following advantages:

the external structure embedded in the granular solids bed brings about no additional dead space.

The DME can be made with a substantially smaller height h, which decreases dead space and thus enables performance to be improved while reducing manufacturing costs.

All the DME embodiments given in this specification have, for example, a total height h of approximately 10 millimeters (mm) to approximately 150 mm, or from approximately 20 mm to approximately 130 mm, and preferably approximately 30 mm to approximately 120 mm. In one particular embodiment, the column has, for each DME, at least one support means 20 (FIG. 8A) such as slats embedded in a granular solids bed downstream of grid 8. In the case shown schematically in FIG. 10A, the DME rests on an external slatted support 20 embedded in the granular solids bed.

Figure 8A:
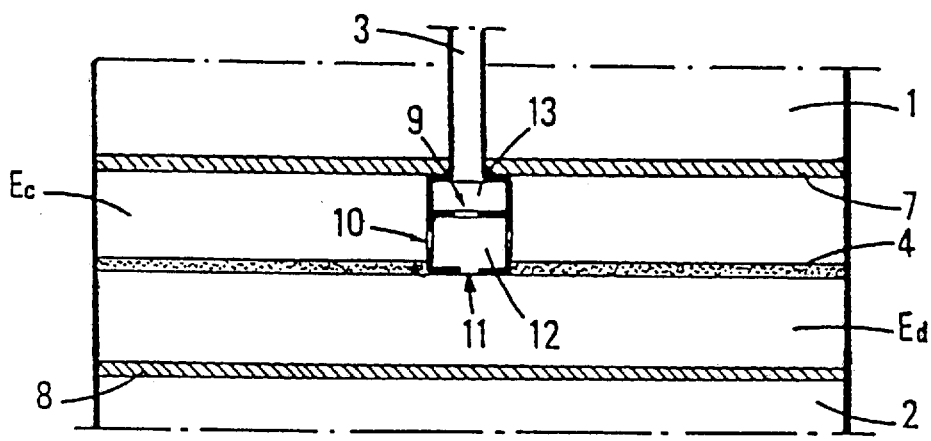
FIGS. 8A and 8B represent different positions of mixing and injection chambers.
Figure 8B:
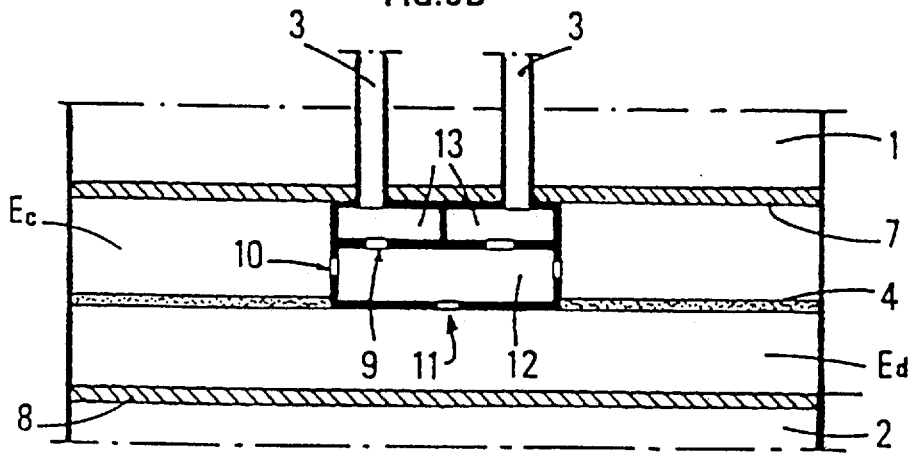

Mixing chambers 12 and the injection and/or removal chamber can also be disposed in different ways shown in FIGS. 8A, 8B.

The injection and/or removal chamber is for example located between two mixing chambers disposed symmetrically as described in relation to FIGS. 5A to 5E.

Another manner of positioning the chambers is shown in FIG. 8A where injection and/or removal chamber 13 is disposed just above at least one mixing chamber 12. Orifices 9 are then located for example in the lower part of injection chamber 13 in order to allow the secondary fluid to pass into mixing chamber 12, the principal fluid introduction orifices being located for example on the sides of the mixing chamber and the mixing outlet orifices in the lower part of the mixing chamber.

The arrangement shown in FIG. 8B and its variants allow in particular secondary fluids B of different composition and quality to be injected and/or removed simultaneously or successively, avoiding risks of contamination by mixing in a feed channel 3 and an injection chamber which are common to the various fluids.

In FIG. 8B, two injection and/or removal chambers 13 are located above a mixing chamber 12. Each of these injection and/or removal chambers has a means 3 of introducing a secondary fluid and orifices 9 allowing the secondary fluid to pass into mixing chambers 12, these orifices being preferably located in the lower wall of chamber 13 which is in contact with mixing chamber 12.

The number of injection and/or removal chambers is not limited to two. It is possible to place several injection and/or removal chambers in the DME, each having its own means of introducing a secondary fluid B, and their own outlet orifices 9, and communicating only with mixing chamber 12. One might thus envisage three injection and/or removal chambers all located above the mixing chamber.

FIGS. 9 and 9A show an example of a DME with two injection and/or removal circuits disposed on either side of the mixing and/or removal chamber.

Each of the two injection and/or removal circuits of at least two secondary fluids B1 and B2 has for example an injection and/or removal chamber 30, 32 respectively, each chamber being connected with a channel 31, 33 for injecting or extracting a secondary fluid. The injection and/or removal chambers 30, 32 are located for example on either side of mixing chamber 37 having for example a substantially elongate shape according to one diameter or according to the largest dimension of the DME.

Injection and/or removal chambers 30, 32 are provided with one or more orifices 35, 36 allowing passage of secondary fluids B1, B2 (removal or injection in the mixing chamber to or from the mixing chamber). These orifices are preferably calibrated orifices.

The dimensions and distribution of orifices 34 for introducing principal fluid A1, outlet orifices 38 from the mixing chamber, and orifices 35, 36 are preferably chosen to obtain a pressure drop and a sufficient flowrate to generate turbulence in mixing chamber 37. In this way, considerable backmixing and better mixing efficiency of principal fluid A1 and secondary fluids B1, B2 are obtained. Such an arrangement thus allows mixing chamber 37 to be isolated from collecting and redistributing spaces Ec and Ed and to minimize direct passage before mixing of secondary fluid flows to these collecting and redistributing spaces.

Inlet orifices 34 of mixing chamber 37 are for example series of holes or slots, preferably regularly spaced to achieve collection of principal fluid A1 to mixing chamber 37 that is as uniform as possible.

The dimensions and geometries of these orifices are chosen so that the fluid entering the mixing chamber acquires a flowrate favorable for creating turbulence in the mixing chamber and at the same time for generating a pressure drop allowing the turbulence to be confined within the mixing chamber.

Thus the space between inlet orifices 34 of fluid A1 is for example between 30 and 150 mm and preferably between 50 and 100 mm. The fluid flowrate through the orifices obtained with such spacing varies for example between 1 and 5 m/s, preferably between 2 and 3 m/s. The pressure drop thus generated at the orifice outlet is between 10 and 100 g/cm$^2$ and preferably between 30 and 60 g/cm$^2$.

The outlets 38 of a fluid from mixing chamber 37 are for example formed by a series of holes or slots preferably regularly spaced in order to redistribute the fluid from the mixing chamber as uniformly as possible to redistributing space Ed. This fluid results from the mixing of at least one principal fluid with at least one secondary fluid for example.

The dimensions of holes or slots 38 are chosen for example to generate a certain pressure drop allowing the mixing turbulence to be confined within mixing chamber 37, for example a pressure drop between 10 and 100 g/cm$^2$ or preferably between 30 and 60 gm$^2$. This pressure drop value corresponds in particular to a hole or slot spacing of 30 to 150 mm and preferably 50 to 100 mm and to a fluid flowrate leaving the mixing chamber of between 1 and 5 m/s and preferably between 2 and 3 m/s.

In this way, the collecting, mixing, and proper distribution of the fluid from the mixing chamber and passing into redistributing space Ed and then through grid 8 when the latter is present are optimized.

Secondary fluid introduction and removal orifices 35, 36 are for example formed by a series of holes, preferably irregularly spaced, for injecting and/or removing secondary fluid B1, B2 in the most uniform possible manner to and/or from mixing chamber 38. These orifices are for example dimensioned so that the linear velocity of the fluid injected at the mixing chamber inlet is sufficiently high to favor creation of turbulence in the mixing chamber and to obtain a significant pressure drop allowing secondary fluid B1 and B2 to be distributed and/or removed as uniformly as possible throughout the injection and/or removal chamber.

The flowrate of the fluid through outlet orifices 35, 36 is for example between 1 and 15 m/s, preferably between 5 and 10 m/s. The hole spacing is chosen to be for example between 30 and 150 mm and preferably between 50 and 100 mm. The corresponding pressure drop ranges between 100 and 2000 g/cm$^2$ and preferably between 200 and 1000 g/cm$^2$.

A mixing chamber 37 has for example a substantially elongate and preferably rectangular shape but can also assume any other shape depending on the geometry of the DME and/or column into which the latter is inserted.

The geometries and dimensions of the injection and/or removal chambers are chosen to ensure a substantially identical fluid flowrate through all the outlet orifices, for example the ratio between the developed length of said chambers and the mean or equivalent width being less than 30 and preferably less than 20 and preferably less than 10.

Advantageously the width of mixing chamber 37 is chosen for example as a function of the value of the flowrate of one of the auxiliary fluids entering the mixing chamber through one of orifices 35, 36 so that the auxiliary fluid encounters the wall of the mixing chamber located opposite the wall from which the auxiliary fluid comes. This optimizes mixing efficiency.

The axes of orifices 35, 36 are staggered with respect to each other as in FIGS. 9A and 10 to avoid injecting an auxiliary fluid into an opposite hole, namely to avoid auxiliary fluids passing into a chamber "not dedicated to them."

The injection and/or removal channels 31, 33 of secondary fluids B1 and B2 respectively to the two injection and/or removal chambers 30, 32 described in FIG. 9 are formed and distributed according to an embodiment shown in FIGS. 11, 12, and 13 for example.

Channel 31 is composed of a small part 31a which passes through column 1 radially, this first part being extended by a second part 31b which passes through the grid and the collecting space (7, Ec) for example in a direction essentially parallel to the lengthwise axis of the column then terminates at the upper wall of the injection and/or removal chamber 30.

Channel 33 which has, for example, a substantially similar geometry, has a first part and a second part and comes up to the lower wall of second chamber 32 through the grid and redistributing space (8, Ed).

According to another embodiment, the number of injection and/or removal circuits is three, distributed on either side of the mixing chamber.

FIG. 14 shows an example of a device with three chambers for injecting and/or removing three secondary fluids B1, B2, and B3 respectively.

Chamber 40 witnesses the passage of a fluid B1 and is disposed for example above chamber 41 which witnesses the passage of a second secondary fluid B2, with these two chambers being on the same side as mixing chamber 37 for example. Each of these chambers 40, 41 communicates with mixing chamber 37 by means of one or more orifices 42, 43 having injection axes that preferably terminate on a solid wall of mixing chamber 37.

On the other side of this mixing chamber 37 is disposed a third injection and/or removal chamber 45 which has, for example, a height identical to the combined height of the two chambers 40 and 41. It communicate with mixing chamber 37 via one or more calibrated orifices 46 whose axis terminates in a solid wall of the chamber.

Due to the respective staggering of the axes of the various orifices 42, 43, and 46, the various secondary fluids B1, B2, and B3 injected into the mixing chamber strike a solid wall, thus mixing better, and direct passage of secondary fluids with different natures into chambers not dedicated to them is avoided.

The other characteristics of the collecting and/or redistributing means are similar to those described in relation to the preceding figures.

The same applies to orifices 34 through which the principal fluid is introduced into the mixing chamber as well as the through-orifices of the various secondary fluids from the injection and/or removal chambers from or to the mixing chamber, and outlet orifices 38.

Of course, chamber 45 of FIG. 2 could be divided into two subchambers while preserving the criterion at the axes of the through-orifices to prevent any mixing of secondary fluids with each other.

Thus, FIG. 15 shows one example of the DME having four injection and/or removal circuits for four secondary fluids B1, B2, B3, and B4 numbered 50, 52, 54, 56 respectively and their associated channels 51, 53, 55, 57.

In this embodiment, the four independent chambers are for example obtained by subdividing chambers 30 and 32 into two subchambers 50, 52 and 54, 56 respectively.

Channels 51, 53 can have shapes and paths similar to those shown in FIG. 11 and reach the two chambers 50, 52 by passing through the upper walls of each of these chambers, with channel 53 passing through chamber 50 along an axis substantially parallel to the axis of the column and over its entire height for example.

Channel 55 passes through one of the lengthwise walls of the column radially to rejoin, along a path with a substantially identical geometry to that of channel 51, the upper wall of chamber 50 while, in this embodiment, channel 57 takes a similar path but rejoins the injection and/or removal chamber 56 at its lower wall.

The staggering of calibrated orifices 58, 59, 60, 61 is such that the majority of secondary fluids injected into the mixing chamber strike one of its solid walls to avoid passage of secondary fluids through orifices communicating with chambers that are not "dedicated" to them.

In certain embodiments of the invention it may be advantageous to have a fifth independent injection and/or removal circuit as shown in FIG. 16.

In this case, the distribution of the injection and/or removal channels with respect to each other and with respect to the column is for example according to one of the embodiments described above.

FIG. 17 shows a DME embodiment where the injection and/or removal circuits are disposed on one side of the mixing chamber. Such an arrangement may be advantageous when the conditions of access to the DME are difficult.

Mixing chamber 70 is located on one side of the DME and has for example a wall in common with one of the lengthwise walls of the column. It is provided on the collecting means side with at least one orifice 71 to allow principal fluid A1 to pass through, with this orifice having for example characteristics substantially similar to those of orifices 34 (FIG. 9), and with one or more calibrated orifices 72 for passage of the mixture having in the same way characteristics substantially identical to the characteristics of orifices 38 (FIG. 9) and located for example in the opposite axis to the orifices introducing fluid into the chamber.

The two chambers 73, 74 for injecting and/or removing the two secondary fluids are located on the same side of mixing chamber 70 with chamber 73 being for example located above chamber 74. They communicate with the outside by channels such as channels 30 not shown for reasons of clarity or by the injection channels shown in FIGS. 11 and 15 (FIG. 9).

These two chambers communicate with mixing chamber 70 by means of one or more orifices 75, 76 determined according to criteria similar to orifices 35 and 36 (FIG. 9) for example.

It is possible to imagine various types of distribution of the secondary fluid injection and/or removal channels in the column.

It goes without saying that, without departing from the framework of the invention, the paths and geometries of the various channels can be adapted according to the following parameters: column geometry, number and geometries of the various chambers, conditions of access to column.

The same applies when their paths through the grids or collecting space are considered, since for example passage through the grid may in certain cases by avoided according to the height of the collecting space.

Figure 28A:
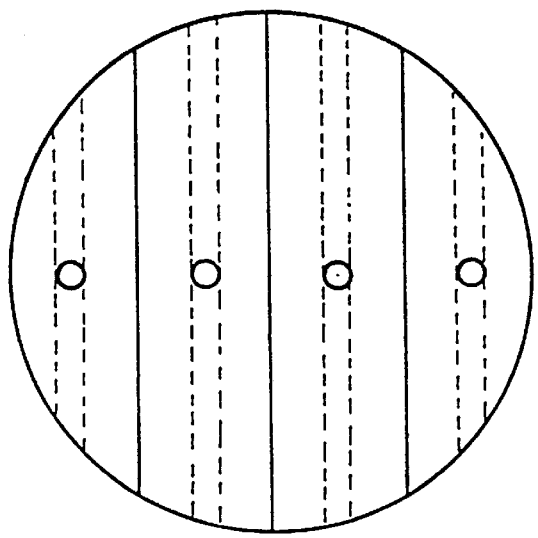
Figure 29A:
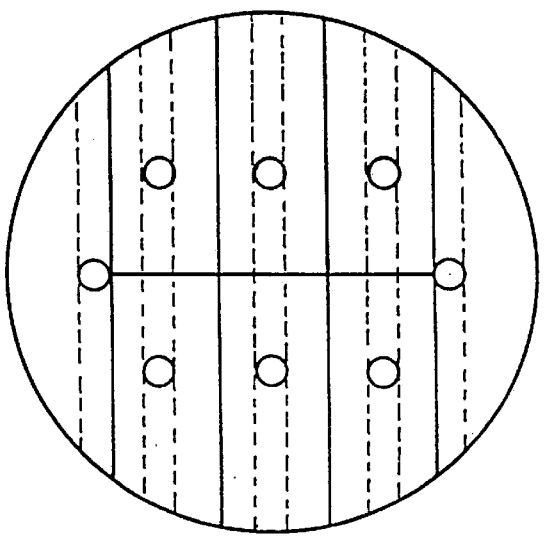
Figure 28B:
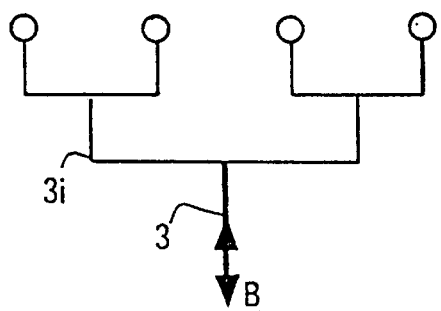
Figure 29B:
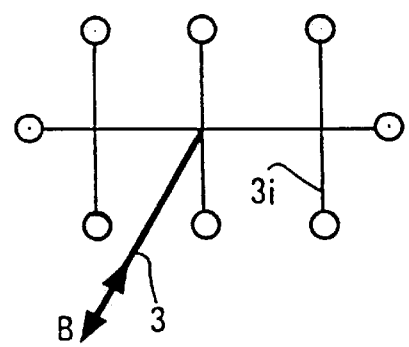
Figure 30A:
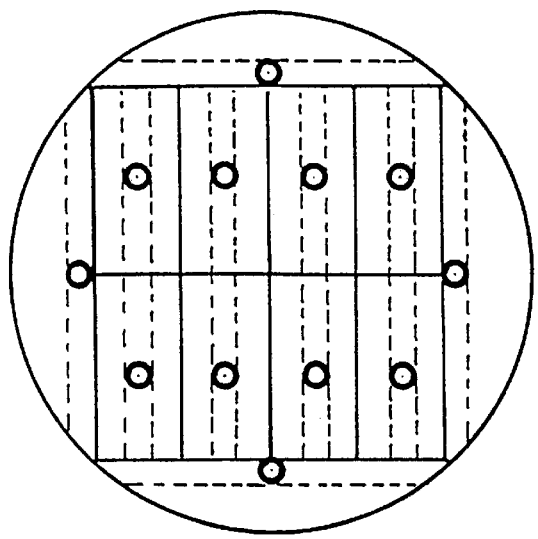
Figure 31A:
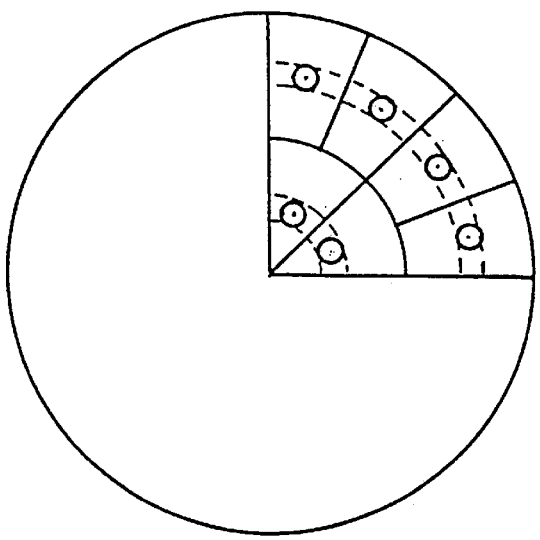
Figure 30B:
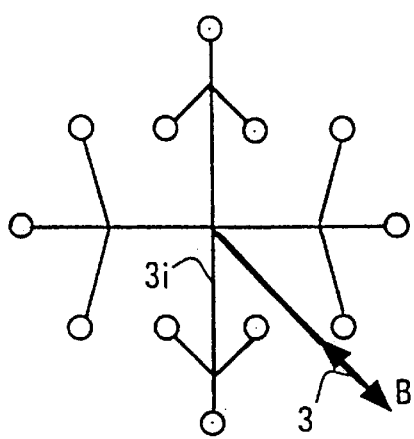
Figure 31B:
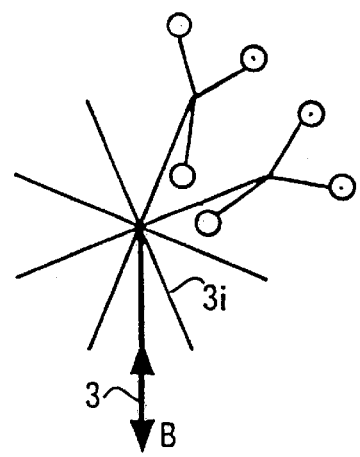

FIGS. 18, 19, 20, and 21 show various possible arrangements for the secondary fluid injection and/or removal channels for columns with several DMEs, for example according to the diagram shown in FIG. 28A.

For columns with several DMEs disposed side by side and or above one another, particularly for columns with large cross sections, the independence of the secondary fluid injection and/or removal chambers may lead to a non-negligible number of channels which can encumber and impede the operation of the device.

In FIGS. 18 to 21, the various channels (Ci, 81$i$, 83$i$) for injecting and/or extracting a secondary fluid of a specified nature join inside the column at the level of a channel or conduit (C, 81, 83). In this case, only principal channel (C, C', 80, 82) traverses the column walls at one or more points.

For example, in FIGS. 18 and 19, channels C and C' for injecting and/or removing fluids B1 and B2 respectively have branches Ci and C'i that distribute the secondary fluids to the dedicated injection and/or removal chambers. "Dedicated chamber" is understood to be the chamber intended to receive one fluid and one fluid alone, in both the secondary fluid removal and injection stages, or possibly fluids that are compatible with each other, i.e. that do not contaminate each other.

In FIG. 19, the column has for example three DMEs, D1, D2, and D3, positioned side by side along the section of the column and each having characteristics substantially identical to those of the DME described in FIG. 9. Each of them has at least one mixing chamber M and two injection and/or extraction chambers I1, I2 located on either side of mixing chamber M.

Principal channels C and C' arrive for example by the upper part of the DME as shown in FIG. 18 horizontally and in a radial direction, for example, and branches Ci and C'i leave principal channels C and C' along a lengthwise axis substantially parallel to the column axis to rejoin the injection and/or removal chambers of type I1, I2 respectively. Of course, without departing from the framework of the invention, the horizontal or vertical arrangement of these channels and their branches as well as their geometry depends on the mode and position of the column; for example the latter can be used horizontally or vertically.

In the same way, it is possible to imagine superimposing principal injection channels C and C' by adapting the shape of the branches coming from the principal channel positioned above the other, or any other variant embodiment.

FIGS. 20, 21 describe a layout for distributing secondary fluids from the periphery of the column.

For a column having, as in FIG. 19, three DMEs disposed side by side, outside channel 80 dedicated to fluid B1 extends inside the column by channel part 81, circular in shape for example over at least part of its length and assuming the shape of the periphery of the DME. Its length is adapted to reach and distribute fluid B1 into all the injection and/or removal chambers I1 dedicated to this fluid through branches, for example pieces of channel 81$i$.

The same applies when fluid B2 injection and/or removal channel is considered, which is distributed through channel 82 extended by the piece of circular channel 83 itself branching off into pieces of channel 83$i$ terminating in the various injection and/or removal chambers.

In FIGS. 20 and 21, the two injection and/or removal channels are shown on parts of the periphery of the column.

This arrangement offers the particular advantage of considerably simplifying the arrangement of the internal connecting channels to the DMEs, while leaving maximum space for the beds of screens or granular solids located on either side of the DME while offering minimum disturbance to circulation of principal fluid A1 through these beds.

The lengths of the circular channels are equal to all or part of the circumference of the column. Moreover these channels can be disposed on top of each other and possibly staggered with respect to each other.

The number of common transverse, rectilinear or nonrectilinear, or peripheral channels is chosen as a function for example of the number of DMEs positioned inside the column and the number of secondary fluids that are desired to be independent.

Due to the independence of the secondary fluid injection and/or removal circuits, the arrangement of the injection and/or removal channel or channels common to the branches can be of any shape without necessitating any constraint of symmetry or residence time.

The examples provided below should not be considered limiting and are intended to show the principal advantages obtained by a DME whose structure has been described above.

Figure 22:
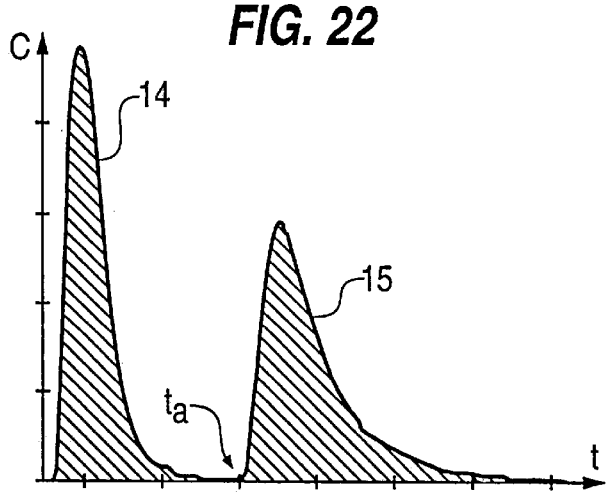
FIG. 22 shows signals representing the distribution of fluid residence-times.
Figure 23A:
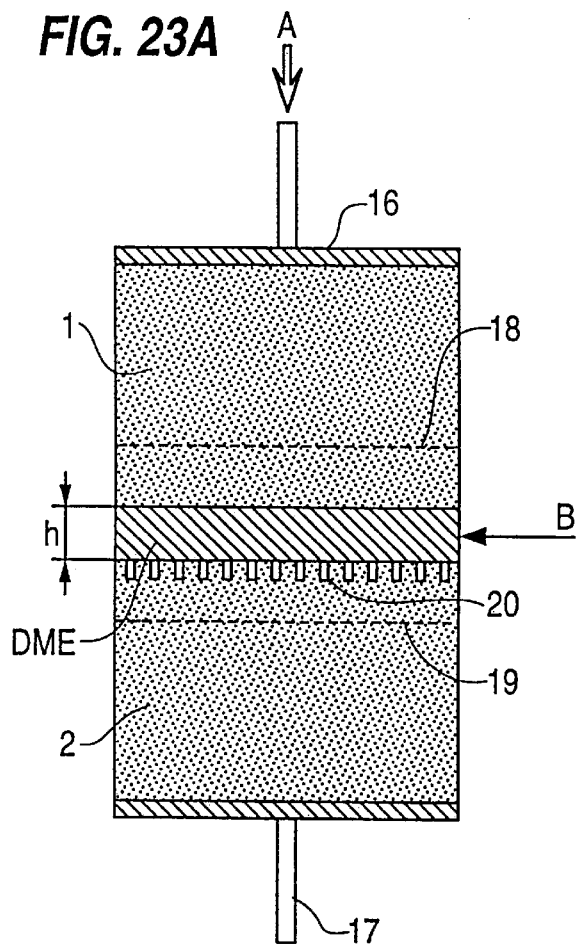
FIG. 23A shows a section through a column with a DME according to the invention.

The efficiency of distribution and mixing and/or removal of the distributor-mixer-extractor is determined for example by measurements of distribution of residence time of the fluids. The principle is described below in connection with FIG. 22: at time t equal to zero, a certain quantity of tracer, hexane for example, is sent into the principal fluid or into the secondary fluid whereby these fluids can be heptane. The shape of the signal obtained is analyzed by measuring the difference of refractive index between the principal fluid such as heptane and hexane. This signal represents input signal 14 (FIG. 22). At a later time, one looks at the shape of output signal 15 (FIG. 22). The parameters considered are the output signal appearance time ta and the area under the curve of the output signal 15 which represents their mean concentration of tracer at a given location. The measurements were made for a column configuration such as that shown in FIG. 23A. The column is comprised of a head distributor 16 of the Amicon type with 1 meter (m) of adsorbent bed 1, of a DME as described above, of 1 meter of absorbent bed 2, and of an Amicon type collector 17. The signals are measured on either side of the DME in sections of column 18 and 19 located at a distance essentially equal to 25 cm from the DME. Six sampling points (a), (b), (c), (d), (e), (f) are provided in section 18 (FIG. 23A) and six sampling points (a'), (b'), (c'), (d'), (e'), (f') in section 19 (FIG. 23C). The adsorbent bed is a bed of granular solids with grains whose particle size ranges from 0.3 mm to 1 mm. This solid is a molecular sieve of the 3 Å (Angstrom) type sold by the CECA Company.

FIGS. 24A, 24B, 25A, 25B and 26A, 26B present the results obtained using a system of the prior art designed according to the specification of U.S. Pat. No. 3,214,247 and the diagram in FIG. 4A of this patent and a DME according to the invention having a mixing chamber 12, and injection and/or removal chamber 13, and a baffle 4 as shown in FIG. 5B.

For all the curves, the abscissa axis represents time and the ordinate axis the concentration of a fluid. The measurements are made at points (a), (b), (c), (d), (e), (f) respectively section (18) (FIG. 23B) and at points (a'), (b'), (c'), (d'), (e'), (f') section (19) (FIG. 23C).

In the examples of FIGS. 24A and 24B and FIGS. 25A and 10B, the tracer is sent by the top of the column (FIG. 23A) in the form of a mixture with the principal fluid. In the first case (FIGS. 24A and 24B), no injection of secondary fluid B and no removal of secondary fluid are effected through the system of the prior art and through the DME according to the invention while in the second case (FIGS. 25A and 25B), a secondary fluid B is injected respectively through the system of the prior art and through the DME according to the invention.

Figure 23B:
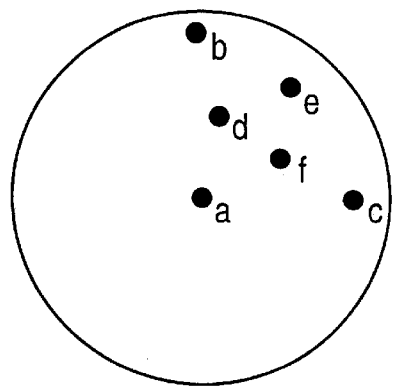
FIGS. 23B and 23C show one example of sampling point positioning.
Figure 23C:
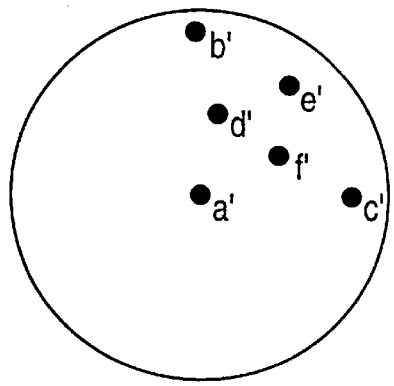

The curves (a), (b), (c), (d), (e), (f), (a'), (b'), (c'), (d'), (e'), (f') correspond to the measurements made at the points with the same numerals as in FIGS. 23B and 23C.

Curves (a), (b), (c), (d), (e), (f) of FIGS. 24A, 24B and 25A, 25B represent the result of the distribution/mixing function of the head distributor from the Amicon Company. These curves are shifted (the times ta are different) by approximately 10 (s) seconds. An imperfect distribution is noted as are areas under the various curves that are not all identical.

Figure 24A:
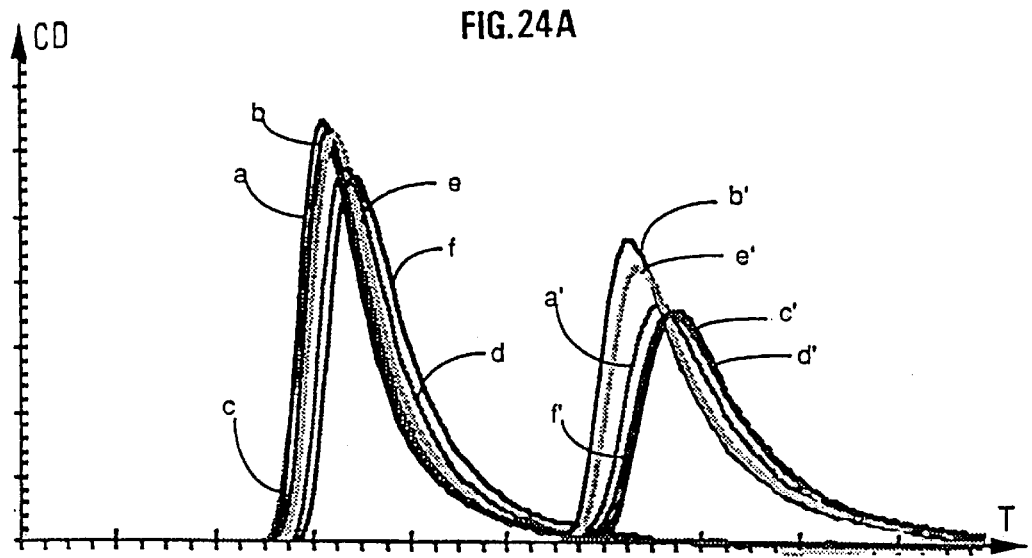
FIGS. 24A, 24B, 25A, 25B, 26A, and 26B show on the same graph the distribution curves of the residence times obtained by means of the DMEs of the prior art and a DME according to the invention.

Curves (a'), (b'), (c'), (d'), (e'), (f') of FIG. 24A show the result of principal fluid A passing through the system of the prior art when no secondary fluid B is injected. The time shift is slightly increased and the disparity of the areas under the various curves likewise. It will be noted that this system interferes with circulation of the principal fluid both at the collecting level and at the redistributing level, and that there is a significant degradation in distribution between the two measuring points.

Figure 24B:
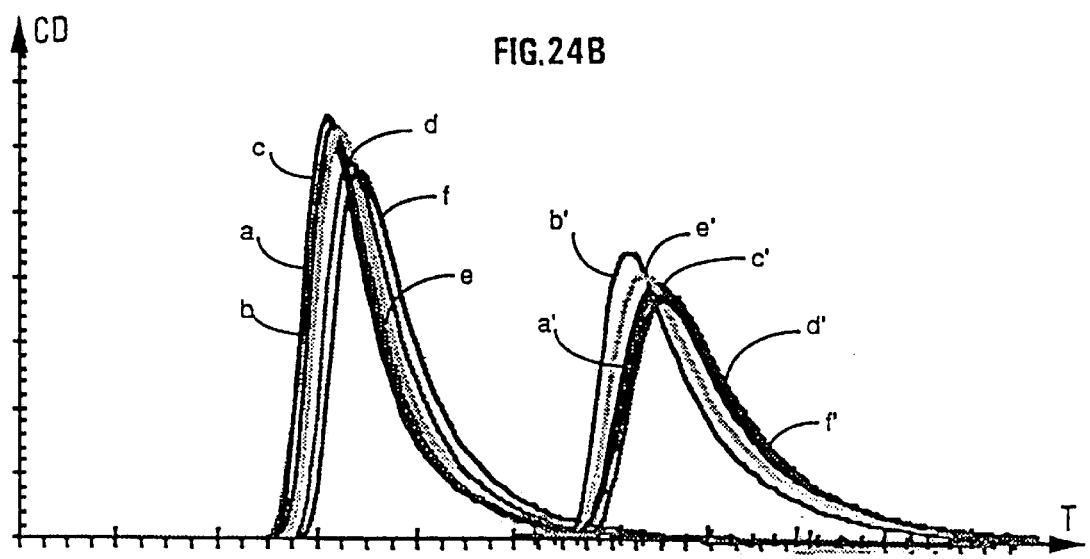

Curves (a'), (b'), (c'), (d'), (e'), (f') of FIG. 24B show the result of principal fluid A passing through the DME according to the invention when no secondary fluid B is injected. The time shift of these curves is the same (or even slightly less) as in the case of curves (a), (b), (c), (d), (f). The difference in the areas under the various curves (a'), (b'), (c'), (d'), (e'), (f') is the same as that obtained with curves (a), (b), (c), (d), (e), (f). The difference in the geometric shapes between curves (a), (b), (c), (d), (e), (f) and curves (a'), (b'), (c'), (d'), (e'), (f') (flattened shape) is essentially due to the natural dispersion caused by the granular solids bed. These curves prove that the use of a DME according to the invention as described above ensures a better collecting and redistributing function with less significant perturbation in principal fluid circulation than in the case of the system of the prior art. Indeed, no significant degradation in distribution between the two measurement points is observed.

Figure 25A:
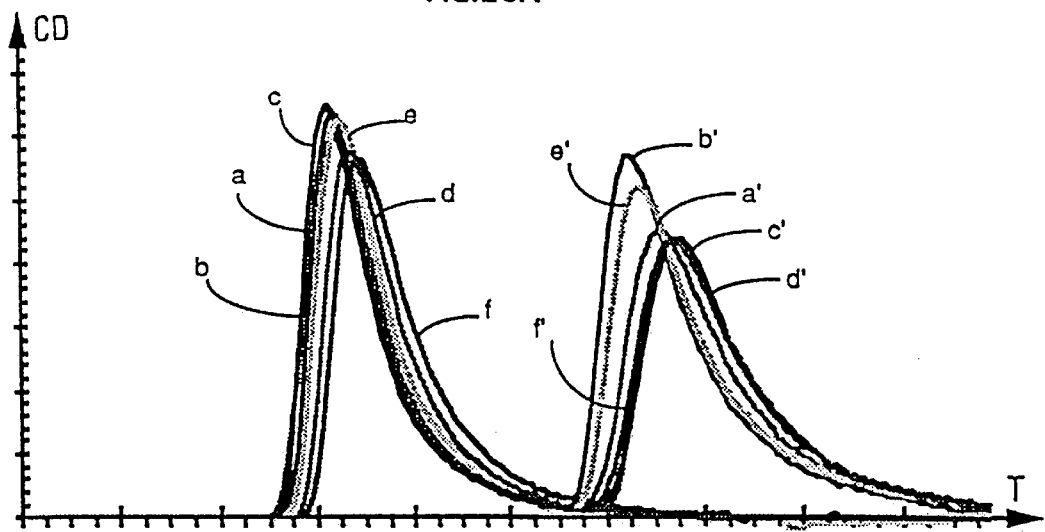
Figure 25B:
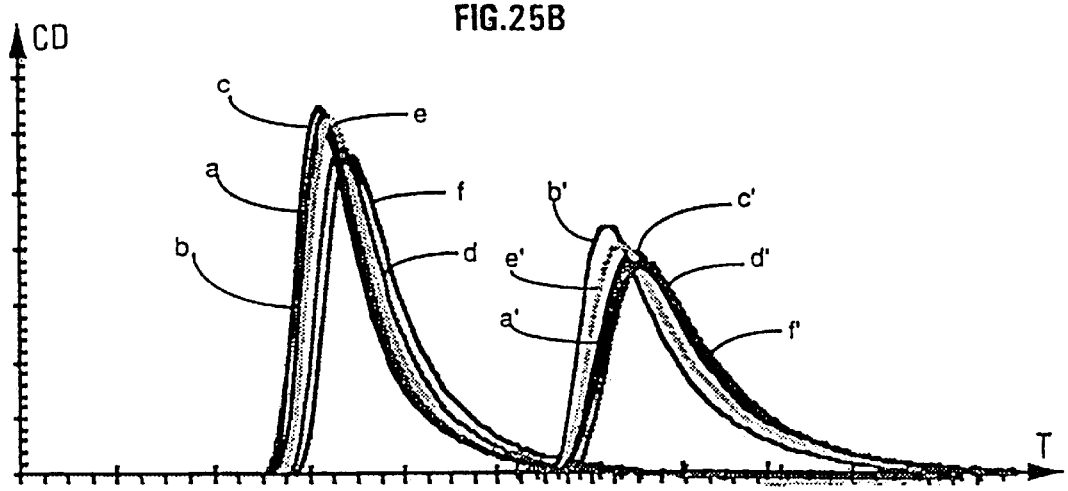

FIGS. 25A and 25B differ from the preceding case due to the fact that the secondary fluid has been injected through the system of the prior art (FIG. 25A) and through the DME according to the invention (FIG. 25B). Examination of the various curves shows that the result is the same as that obtained from analyzing the preceding curves. The DME according to the invention has less perturbing effect on circulation of the principal fluid and ensures a better mixing function.

Figure 26A:
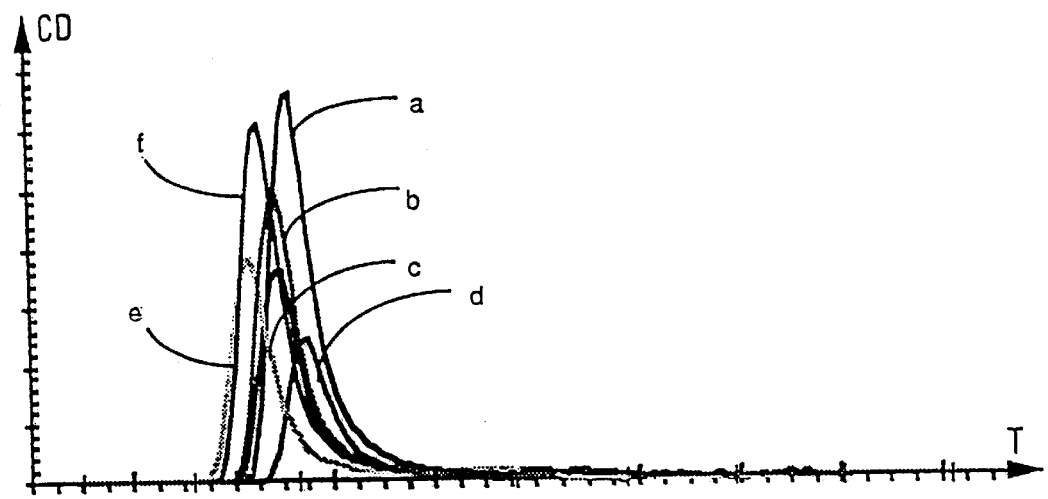
Figure 26B:
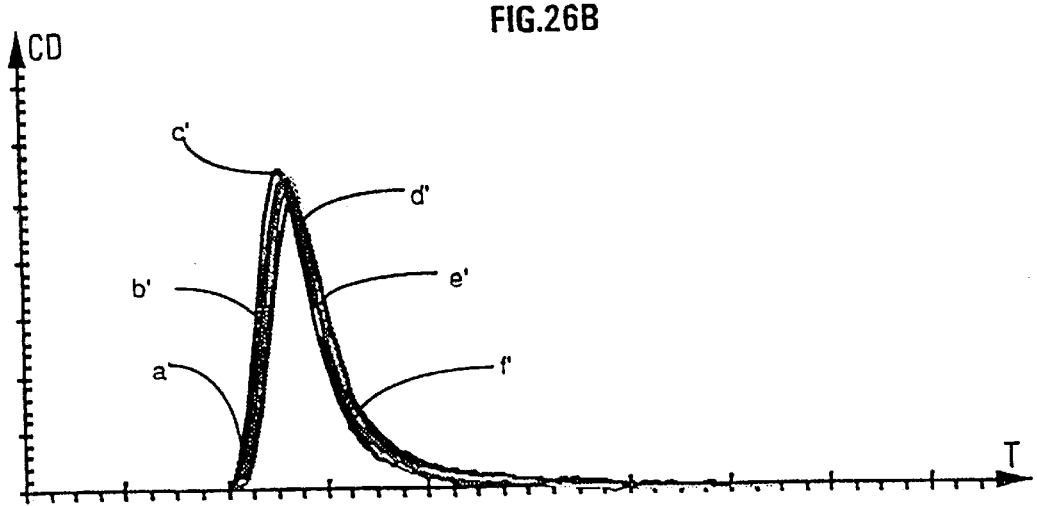

FIGS. 26A and 26B present the result of measurements obtained when a tracer is injected into secondary fluid B, with principal fluid A circulating normally in the column, when the system of the prior art (FIG. 26A) and a DME according to the invention (FIG. 26B) respectively are used.

In FIG. 26A it appears clearly that the signals do not all appear simultaneously and that the mean concentration, corresponding to the area under each of the curves of each of the signals is different, showing that the mixture is of a poor quality. In FIG. 26B, the signals appear almost simultaneously and the mean concentration is identical and the mixing uniform at all points.

These three examples of curves show the advantages offered by the DME having a mixing chamber and an injection and/or removal chamber as described above.

The DMEs made according to the invention can assume various forms while keeping the same operating principles.

FIGS. 27A to 27E describe different DME shapes, rectangular, polygonal, sectoral, and segmentary, respectively, provided indicatively and not limitively.

The mixing and injection chambers (shown in dashed lines in the figures) have for example a substantially elongate shape, generally rectilinear (FIGS. 27A, 27B, 27C$_1$, 27C$_3$, and 27E) or curved (27C$_2$, 27D).

Figure 27A:
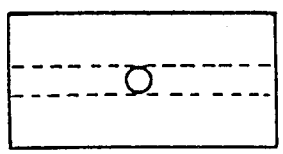
FIGS. 27A, 27B, 27C, 27D, and 27E show schematically various DME forms and, FIGS. 28A, 28B, 29A, 29B, 30A, 30B, 31A and 31B show examples of the disposition of several DMEs according to the invention in a column.
Figure 27B:
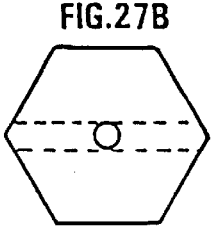
Figure 27C:
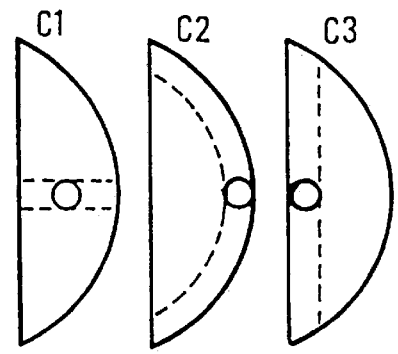
Figure 27D:
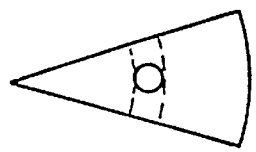
Figure 27E:
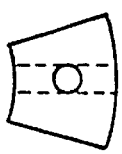

These chambers are for example disposed essentially in the middle of the DME (FIGS. 27A, 27B, 27C$_1$, 27D, 27E) or on one side (FIG. 27C$_2$, 27C$_3$).

The maximum size of a circular or polygonal DME may vary and reach a diameter of at least 1.5 cm, with this diameter being as much as 2 m. For other shapes, for example the rectangular and segmentary shapes, the maximum size can be as large as 3 or 4 m in length and 1.5 to 8 m in width.

In the case of granular beds with very large sections, for example greater in size than the maximum sizes referred to above with reference to the circular and rectangular shapes, the quality of mixing and of distribution may deteriorate when a single DME is used. It is then possible to use several DMEs positioned side by side in order for example to cover the entire section of the bed, each DME thus having a size less than the maximum size. Such an arrangement leads to good mixing and distribution for each subsection thus defined having the qualities referred to with respect to the DME described for example in FIG. 5A.

Several examples of arrangements of several DMEs and their fluid supply mode are given in FIGS. 28A, 28B, 29A, 29B, 30A, 30B, 31A, 31B indicatively and not limitively.

In all the embodiments, using several DMEs disposed side by side, the secondary fluid B injection and removal means are designed for example to supply all the DMEs as uniformly and isochronously as possible. This may be achieved for example by providing at least one symmetry of distribution and one isolength, particularly of injection means 3 and their branches 3i allowing injection of secondary fluid to the various DMEs (FIGS. 28B, 29B, 30B, 31B).

In the case where several secondary fluids B are injected or removed in a single DME or a set of several DMEs located side by side, the number of injection means 3 and their branches 3i is preferably equal to the number of secondary fluids injected into the DME. These injection means and their branch means are preferably independent of each other.

Of course, the examples and figures described above are only nonlimiting examples of the invention. Any individual skilled in the art would be able to make various modifications and/or additions to the DME and the column, the description of which is provided on a nonlimiting basis without departing from the framework of the invention.

We claim:

1. Column having at least a first bed (1) and at least a second bed (2) of granular solids separated from each other by at least one distributor-mixer-extractor, each distributor-mixer-extractor comprising in combination:

at least one injection and/or removal channel (3) of a secondary fluid or second fluid, said channel (3) being connected to at least one injection or removal chamber or first chamber (13), said first chamber having at least one passage opening (9) in at least one of its walls, one or more means (7) for collecting a principal fluid, at least one mixing chamber (12) or second chamber located in the vicinity of said first chamber (13) and communicating with the latter by at least one passage opening (9), said second chamber (12) having one or more orifices (10) allowing passage of said second fluid coming from said collecting means (7) or to said collecting means and at least one passage (11) for a fluid coming from the mixing chamber, at least one or more means (8) of redistributing said fluid coming from said mixing chamber to the second bed of granular solids, a baffle (4) located;

relative to the collecting means (7) and to the mixing chamber (12) to create a collecting space (Ec) communicating with said opening (10), relative to said distributing means (8) and to said mixing chamber (12) to create a space (Ed) for redistributing said fluid coming from the mixing chamber, said redistributing space (Ed) communicating with said passage (11), and said baffle being located such as to separate said collecting and redistributing spaces, characterized in that at least one of the fluid passages (11) has at least one calibrated orifice having a geometry designed to create a sufficient pressure drop to confine fluid turbulence inside said mixing chamber, wherein the first grid (7) is substantially in contact with the first bed and the second grid (8) is substantially in contact with the second bed.

2. Column according to claim 1, characterized in that the first and second grid (7, 8) cover respectively substantially the totality of the section of the first bed and substantially the totality of the section of the second bed.

3. Column according to claim 1, characterized in that said injection and/or removal channels connecting each of said injection and/or removal chambers are joined in a principal channel inside said column.

4. Column according to one of claim 1, characterized in that each distributor-mixer-extractor has at least one external support means embedded in the granular solids bed downstream of second grid (8) of the distributor-mixer-extractor.

5. Column according to claim 4 wherein the external support means is of the slatted or equivalent type.

* * * * *